(12) United States Patent  
Greene

(10) Patent No.: US 8,140,151 B2
(45) Date of Patent: Mar. 20, 2012

(54) IMPLANTABLE SEIZURE MONITOR

(75) Inventor: David Greene, Fort Wayne, IN (US)

(73) Assignee: NeuroPace, Inc., Mountain View, CA (US)

( * ) Notice: Subject to any disclaimer, the term of this patent is extended or adjusted under 35 U.S.C. 154(b) by 169 days.

(21) Appl. No.: 12/770,697

(22) Filed: Apr. 29, 2010

(65) Prior Publication Data

US 2011/0004116 A1    Jan. 6, 2011

Related U.S. Application Data

(63) Continuation of application No. 11/371,701, filed on Mar. 8, 2006, now Pat. No. 7,787,945.

(51) Int. Cl.
A61B 5/04    (2006.01)
(52) U.S. Cl. .................................. 600/544; 600/545
(58) Field of Classification Search ........... 600/544–545
See application file for complete search history.

(56) References Cited

U.S. PATENT DOCUMENTS

| | | | |
|---|---|---|---|
| 4,566,464 A | 1/1986 | Piccone et al. | |
| 5,857,978 A | 1/1999 | Hively et al. | |
| 5,995,868 A | 11/1999 | Dorfmeister et al. | |
| 6,006,124 A | 12/1999 | Fischell et al. | |
| 6,016,449 A | 1/2000 | Fischell et al. | |
| 6,018,682 A | 1/2000 | Rise | |
| 6,201,980 B1 | 3/2001 | Darrow et al. | |
| 6,466,822 B1 | 10/2002 | Pless et al. | |
| 6,473,639 B1 | 10/2002 | Fischell et al. | |
| 6,594,524 B2 | 7/2003 | Esteller et al. | |
| 6,647,296 B2 | 11/2003 | Fischell et al. | |
| 6,726,678 B1 | 4/2004 | Nelson et al. | |
| 6,810,285 B2 * | 10/2004 | Pless et al. | 600/544 |
| 7,136,695 B2 | 11/2006 | Pless et al. | |
| 7,174,206 B2 | 2/2007 | Frei et al. | |
| 7,177,674 B2 | 2/2007 | Echauz et al. | |
| 7,277,748 B2 | 10/2007 | Wingeier et al. | |
| 2003/0004428 A1 | 1/2003 | Pless et al. | |
| 2003/0028229 A1 | 2/2003 | Rothman | |
| 2003/0074033 A1 | 4/2003 | Pless et al. | |
| 2003/0144711 A1 | 7/2003 | Pless et al. | |
| 2004/0054297 A1 | 3/2004 | Wingeier et al. | |
| 2004/0092801 A1 | 5/2004 | Drakulic | |
| 2004/0133119 A1 | 7/2004 | Osorio et al. | |
| 2004/0138518 A1 | 7/2004 | Rise et al. | |

(Continued)

FOREIGN PATENT DOCUMENTS

GB    2406381    3/2005

OTHER PUBLICATIONS

Cyberonics, Inc., www.vnstherapy.com NeuroCyberonic Prosthesis (NCP)).

(Continued)

*Primary Examiner* — Patricia Mallari
*Assistant Examiner* — Michael D'Angelo

(57) ABSTRACT

An implantable seizure monitor can include at least one sensing electrode and an electronics module configured to detect, record and/or log neurological events. For example, the electronics module can be configured to detect brainwaves indicative of seizures, such as, for example, epileptic seizures, and to create a log indicating when such seizures occur. The implantable seizure monitor can include a cushioning member made of a soft material and configured to be implantable between the epidermis and cranium of a patient.

11 Claims, 31 Drawing Sheets

U.S. PATENT DOCUMENTS

2006/0111644 A1 5/2006 Guttag et al.
2006/0129056 A1 6/2006 Leuthardt et al.
2006/0287691 A1 12/2006 Drew
2007/0016094 A1 1/2007 Pless

OTHER PUBLICATIONS

Medtronic, Inc., www.activadbs.comlabout_activa.asp.

Medtronic (2003) "Your Activa (tm) Therapy (With a Kinetra (trn) or Soletra (trn) Neurostimulator," Patient Manual.

Gotrnan, J, "Automatic Seizure Detection: Improvements and Evaluation," Electroencephalogr. and Clinical Neurophysiol. (1990) 76(4):317-24.

Qu, R., et al., "A Seizure Warning System for Long-Term Epilepsy Monitoring," Neurology (1995) 45: 2250-4.

Qu, R., et al., "A Patient-Specific Algorithm for the Detection of Seizure Onset in Long-Term EEG Monitoring: Possible Use As a Warning Device," IEEE Transactions on Biomedical Engineering (1997) 44(2): II5-22.

Wagner, R.R., "Suppression of Cortical Epileptiform Activity by Generalized and Localized ECoG Desynchronization," Electroencephalogr. and Clinical Neurophysiol. (1975) 39(5): 499-506.

* cited by examiner iSM Seizure Report

Patient: John Doe

Physician: Jane Smith, MD

Date of Report: xx-xx-xxxx

Date Range: x-x-xxxx to xx-xx-xxxx

Event Log
A = Discontinue Carbamazepine
B = Begin Zonisamide 200 mg BID

IMPLANTABLE SEIZURE MONITOR

RELATED APPLICATIONS

This application is a continuation application of U.S. patent application Ser. No. 11/371,701, entitled "Implantable Seizure Monitor" filed Mar. 8, 2006, which is incorporated by reference herein in its entirety.

BACKGROUND OF THE INVENTIONS

1. Field of the Inventions

The inventions disclosed herein are directed to devices for detecting brainwaves, and more particularly, devices for detecting and logging neurological events indicative of seizures.

2. Description of the Related Art

Epilepsy, a neurological disorder characterized by the occurrence of seizures (specifically episodic impairment or loss of consciousness, abnormal motor phenomena, psychic or sensory disturbances, or the perturbation of the autonomic nervous system), is debilitating to a great number of people. It is believed that as many as two to four million Americans may suffer from various forms of epilepsy. Research has found that its prevalence may be even greater worldwide, particularly in less economically developed nations, suggesting that the worldwide figures for epilepsy sufferers may be in excess of one hundred million.

Because epilepsy is characterized by seizures, its sufferers are frequently limited in the kinds of activities they may participate in. Epilepsy can prevent people from driving, working, or otherwise participating in much of what society has to offer. Some epilepsy sufferers have serious seizures so frequently that they are effectively incapacitated.

Furthermore, epilepsy is often progressive and can be associated with degenerative disorders and conditions. Over time, epileptic seizures often become more frequent and more serious, and in particularly severe cases, are likely to lead to deterioration of other brain functions (including cognitive function) as well as physical impairments.

The current state of the art in treating neurological disorders, particularly epilepsy, typically involves drug therapy and surgery. The first approach is usually drug therapy.

A number of drugs are approved and available for treating epilepsy, such as sodium valproate, phenobarbital/primidone, ethosuximide, gabapentin, phenytoin, and carbamazepine, as well as a number of others. Unfortunately, those drugs typically have serious side effects, especially toxicity, and it is extremely important in most cases to maintain a precise therapeutic serum level to avoid breakthrough seizures (if the dosage is too low) or toxic effects (if the dosage is too high). The need for patient discipline is high, especially when a patient's drug regimen causes unpleasant side effects the patient may wish to avoid.

Moreover, while many patients respond well to drug therapy alone, a significant number (at least 20-30%) do not. For those patients, surgery is presently the best-established and most viable alternative course of treatment.

Currently practiced surgical approaches include radical surgical resection such as hemispherectomy, corticectomy, lobectomy and partial lobectomy, and less-radical lesionectomy, transection, and stereotactic ablation. Besides being less than fully successful, these surgical approaches generally have a high risk of complications, and can often result in damage to eloquent (i.e., functionally important) brain regions and the consequent long-term impairment of various cognitive and other neurological functions. Furthermore, for a variety of reasons, such surgical treatments are contraindicated in a substantial number of patients. And unfortunately, even after radical brain surgery, many epilepsy patients are still not seizure-free.

Electrical stimulation is an emerging therapy for treating epilepsy. However, currently approved and available electrical stimulation devices apply continuous electrical stimulation to neural tissue surrounding or near implanted electrodes, and do not perform any detection—they are not responsive to relevant neurological conditions.

The NeuroCybernetic Prosthesis (NCP) from Cyberonics, for example, applies continuous electrical stimulation to the patient's vagus nerve. This approach has been found to reduce seizures by about 50% in about 50% of patients. Unfortunately, a much greater reduction in the incidence of seizures is needed to provide clinical benefit. Medtronic presently offers several DBS systems, including the Activa, Solectra, and Kinetra systems. The Activa system includes a pectorally implanted continuous deep brain stimulator intended primarily to treat Parkinson's disease. In operation, it supplies a continuous electrical pulse stream to a selected deep brain structure where an electrode has been implanted.

Continuous stimulation of deep brain structures for the treatment of epilepsy has not met with consistent success. To be effective in terminating seizures, it is believed that one effective site where stimulation should be performed is near the focus of the epileptogenic region. The focus is often in the neocortex, where continuous stimulation may cause significant neurological deficit with clinical symptoms including loss of speech, sensory disorders, or involuntary motion. Accordingly, research has been directed toward automatic responsive epilepsy treatment based on a detection of imminent seizure.

A typical epilepsy patient experiences episodic attacks or seizures, which are generally electrographically defined as periods of abnormal neurological activity. As is traditional in the art, such periods shall be referred to herein as "ictal".

Most prior work on the detection and responsive treatment of seizures via electrical stimulation has focused on analysis of electroencephalogram (EEG) and electrocorticogram (ECoG) waveforms. In general, EEG signals represent aggregate neuronal activity potentials detectable via electrodes applied to a patient's scalp. ECoG signals, deep-brain counterparts to EEG signals, are detectable via electrodes implanted on or under the dura mater, and usually within the patient's brain. Unless the context clearly and expressly indicates otherwise, the term "EEG" shall be used generically herein to refer to both EEG and ECoG signals.

Much of the work on detection has focused on the use of time-domain analysis of EEG signals. See, e.g., J. Gotman, Automatic seizure detection: improvements and evaluation, Electroencephalogr. Clin. Neurophysiol. 1990; 76(4): 317-24. In a typical time-domain detection system, EEG signals are received by one or more implanted electrodes and then processed by a control module, which then is capable of performing an action (intervention, warning, recording, etc.) when an abnormal event is detected.

It is generally preferable to be able to detect and treat a seizure at or near its beginning, or even before it begins. The beginning of a seizure is referred to herein as an "onset." However, it is important to note that there are two general varieties of seizure onsets. A "clinical onset" represents the beginning of a seizure as manifested through observable clinical symptoms, such as involuntary muscle movements or neurophysiological effects such as lack of responsiveness. An "electrographic onset" refers to the beginning of detectable electrographic activity indicative of a seizure. An electrographic onset will frequently occur before the corresponding clinical onset, enabling intervention before the patient suffers symptoms, but that is not always the case. In addition, there are changes in the EEG that occur seconds or even minutes before the electrographic onset that can be identified and used to facilitate intervention before electrographic or clinical onsets occur. This capability would be considered seizure prediction, in contrast to the detection of a seizure or its onset.

In the Gotman system, EEG waveforms are filtered and decomposed into "features" representing characteristics of interest in the waveforms. One such feature is characterized by the regular occurrence (i.e., density) of half-waves exceeding a threshold amplitude occurring in a specified frequency band between approximately 3 Hz and 20 Hz, especially in comparison to background (non-ictal) activity. When such half-waves are detected, it is believed that seizure activity is occurring For related approaches, see also H. Qu and J. Gotman, A seizure warning system for long term epilepsy monitoring, Neurology 1995; 45: 2250-4; and H. Qu and J. Gotman, A Patient-Specific Algorithm for the Detection of Seizure Onset in Long-Term EEG Monitoring: Possible Use as a Warning Device, IEEE Trans. Biomed. Eng. 1997; 44(2): 115-22.

The Gotman articles address half wave characteristics in general, and introduce a variety of measurement criteria, including a ratio of current epoch amplitude to background; average current epoch EEG frequency; average background EEG frequency; coefficient of variation of wave duration; ratio of current epoch amplitude to following time period; average wave amplitude; average wave duration; dominant frequency (peak frequency of the dominant peak); and average power in a main energy zone. These criteria are variously mapped into an n-dimensional space, and whether a seizure is detected depends on the vector distance between the parameters of a measured segment of EEG and a seizure template in that space.

It should be noted that the schemes set forth in the above articles are not tailored for use in an implantable device, and hence typically require more computational ability than would be available in such a device.

U.S. Pat. No. 6,018,682 to Rise describes an implantable seizure warning system that implements a form of the Gotman system. However, the system described therein uses only a single detection modality, namely a count of sharp spike and wave patterns within a timer period. This is accomplished with relatively complex processing, including averaging over time and quantifying sharpness by way of a second derivative of the signal. The Rise patent does not disclose how the signals are processed at a low level, nor does it explain detection criteria in any sufficiently specific level of detail.

A more computationally demanding approach is to transform EEG signals into the frequency domain for rigorous spectrum analysis. See, e.g., U.S. Pat. No. 5,995,868 to Dorfineister et al., which analyzes the power spectral density of EEG signals in comparison to background characteristics. Although this approach is generally believed to achieve good results, for the most part, its computational expense renders it less than optimal for use in long-term implanted epilepsy monitor and treatment devices. With current technology, the battery life in an implantable device computationally capable of performing the Dorfineister method would be too short for it to be feasible.

Also representing an alternative and more complex approach is U.S. Pat. No. 5,857,978 to Hively et al., in which various non-linear and statistical characteristics of EEG signals are analyzed to identify the onset of ictal activity. Once more, the calculation of statistically relevant characteristics is not believed to be feasible in an implantable device.

U.S. Pat. No. 6,016,449 to Fischell, et al. (which is hereby incorporated by reference as though set forth in full herein), describes an implantable seizure detection and treatment system. In the Fischell et al. system, various detection methods are possible, all of which essentially rely upon the analysis (either in the time domain or the frequency domain) of processed EEG signals. Fischell's controller is preferably implanted intracranially, but other approaches are also possible, including the use of an external controller. When a seizure is detected, the Fischell system applies responsive electrical stimulation to terminate the seizure, a capability that will be discussed in further detail below.

All of these approaches provide useful information, and in some cases may provide sufficient information for accurate detection and prediction of most imminent epileptic seizures.

However, none of the various implementations of the known approaches provide 100% seizure detection accuracy in a clinical environment.

Two types of detection errors are generally possible. A "false positive," as the term is used herein, refers to a detection of a seizure or ictal activity when no seizure or other abnormal event is actually occurring. Similarly, a "false negative" herein refers to the failure to detect a seizure or ictal activity that actually is occurring or shortly will occur.

In most cases, with all known implementations of the known approaches for detecting abnormal seizure activity solely by monitoring and analyzing EEG activity, when a seizure detection algorithm is tuned to catch all seizures, there will be a significant number of false positives. While it is currently believed that there are minimal or no side effects to limited amounts of over-stimulation (e.g., providing stimulation sufficient to terminate a seizure in response to a false positive), the possibility of accidentally initiating a seizure or increasing the patient's susceptibility to seizures must be considered.

As is well known, it has been suggested that it is possible to treat and terminate seizures by applying electrical stimulation to the brain. See, e.g., U.S. Pat. No. 6,016,449 to Fischell et al., and H. R. Wagner, et al., Suppression of cortical epileptiform activity by generalized and localized ECoG desynchronization, Electroencephalogr. Clin. Neurophysiol. 1975; 39(5): 499-506. And as stated above, it is believed to be beneficial to perform this stimulation only when a seizure (or other undesired neurological event) is occurring or about to occur, as inappropriate stimulation may result in the initiation of seizures.

Furthermore, it should be noted that a false negative (that is, a seizure that occurs without any warning or treatment from the device) will often cause the patient significant discomfort and detriment. Clearly, false negatives are to be avoided.

It has been found to be difficult to achieve an acceptably low level of false positives and false negatives with the level of computational ability available in an implantable device with reasonable battery life.

Preferably, the battery in an implantable device, particularly one implanted intracranially, should last at least several years. There is a substantial risk of complications (such as infection, blood clots, and the overgrowth of scar tissue) and lead failure each time an implanted device or its battery is replaced.

As stated above, the detection and prediction of ictal activity has traditionally required a significant amount of computational ability. Moreover, for an implanted device to have significant real-world utility, it is also advantageous to include a number of other features and capabilities. Specifically, treatment (via electrical stimulation or drug infusion) and/or warning (via an audio annunciator, for example), recording of EEG signals for later consideration and analysis, and telemetry providing a link to external equipment are all useful capabilities for an implanted device capable of detecting or predicting epileptiform signals. All of these additional subsystems will consume further power.

Moreover, size is also a consideration. For various reasons, intracranial implants are favored. A device implanted intracranially (or under the scalp) will typically have a lower risk of failure than a similar device implanted pectorally or elsewhere, which require a lead to be run from the device, through the patient's neck to the electrode implantation sites in the patient's head. This lead is also prone to receive additional electromagnetic interference.

As is well known in the art, the computational ability of a processor-controlled system is directly related to both size and power consumption. In accordance with the above considerations, therefore, it would be advantageous to have sufficient detection and prediction capabilities to avoid a substantial number of false positive and false negative detections, and yet consume little enough power (in conjunction with the other subsystems) to enable long battery life. Such an implantable device would have a relatively low-power central processing unit to reduce the electrical power consumed by that portion.

More recently, as described in U.S. Pat. No. 6,810,285, issued to Pless et al., implantable devices have been developed which provide both detection/prediction of ictal activity and electrostimulation for attenuating or stopping an epileptic seizure. These devices are implanted firstly by performing a craniotomy in which a portion of the skull is cut away and then mounting the device in the empty space left after the craniotomy. Electrodes that are connected to the implant device are implanted onto the surface of or into the brain lobes at a depth of up to about 1 to 2 cm. These electrodes are used for the detection of ictal activity as well as the delivery of electrostimulation.

In order to identify the preferred implantation sites for the electrodes, it is advantageous to record a patient's brainwaves, and more particularly, brainwaves indicative of ictal activity, to identify the area from which the ictal brainwaves originate. Further, it is advantageous to identify the frequency of a patient's ictal activity in order to optimize the device that is eventually implanted into the patient's brain matter.

One persistent hurdle that remains in the precise diagnosis and understanding of a particular patient's form of epilepsy is the patient's memory regarding his or her own seizure activity. For example, an epileptic patient can have seizures while they are awake, yet completely forget the seizure ever occurred. Further, epileptic patients can also have seizures during sleep, and thus, never have an opportunity to form a memory of the seizure.

SUMMARY OF THE INVENTIONS

An aspect of at least one of the embodiments disclosed herein includes the realization that the diagnosis and the adaptation of a treatment for an epileptic patient can be enhanced by providing a patient with an implantable seizure monitor that is, for example, configured to detect and/or record brainwaves indicative of ictal activity.

In some embodiments, the device can be implanted between the epidermis and the skull. As such, a craniotomy is not required to implant the device, thus reducing the complexity of the implantation procedure and reducing the risks of surgery. Further, the patient can have the benefit of objective and reliable recording and/or logging of ictal events without the need for external wire leads which may be inconvenient or embarrassing for a patient.

In some embodiments, the device can include a processor and a power supply mounted within a housing and a cushioning material in which the housing is suspended. Sensors for detecting brainwaves can be suspended in the cushioning material and connected to the housing with leads. As such, the device can be comfortably implanted between the epidermis and the cranium. Additionally, this arrangement allows the sensors to be spaced apart to provide better directional detection of the ictal brainwaves and allows the size of the housing to be reduced.

Thus, in accordance with an aspect of at least one of the embodiments disclosed herein, an implantable recording device for detecting and logging neurological events is provided. The recording device can include a housing enclosing at least one electronic module and at least a first sensing electrode connected to the electronic module. Additionally, the recording device can comprise a cushioning member surrounding at least three sides of each of the housing and the at least one sensing electrode, the cushioning member being made from a soft biocompatible material.

In accordance with an aspect of at least another of the embodiments disclosed herein, a method of monitoring a seizure disorder of an animal is provided. The method can include implanting a seizure monitor between the epidermis and cranium of the animal, wherein the seizure monitor can include a housing enclosing an electronic module configured to detect and log seizure events, at least first and second sensing electrodes, and the cushioning member surrounding at least three sides of each of the housing and the sensing electrodes.

In accordance with an aspect of at least a further embodiment, an implantable device for detecting neurological events can be provided. The device can comprise at least one sensor configured to detect brainwaves and to generate a signal indicative of the brainwaves. An amplifier can be configured to amplify signal from the sensor. Additionally, an event detector can be configured to determine if a neurological event has occurred based on the saturation of the amplifier.

BRIEF DESCRIPTION OF THE DRAWINGS

These and other objects, features, and advantages of the inventions will become apparent from the detailed description below and the accompanying drawings, in which.

DETAILED DESCRIPTION OF THE INVENTIONS

The inventions described herein, with reference to detailed illustrative and exemplary embodiments, are described in the context of an implant disposed between the epidermis and skull of a human patient. However, the inventions disclosed herein can be used in other context as well. It is apparent from the description provided below that the systems, apparatuses, and methods can be embodied in a wide variety of forms. Consequently, the specific structural and functional details disclosed herein are only representative and do not limit the scope of the inventions.

Figure 1:
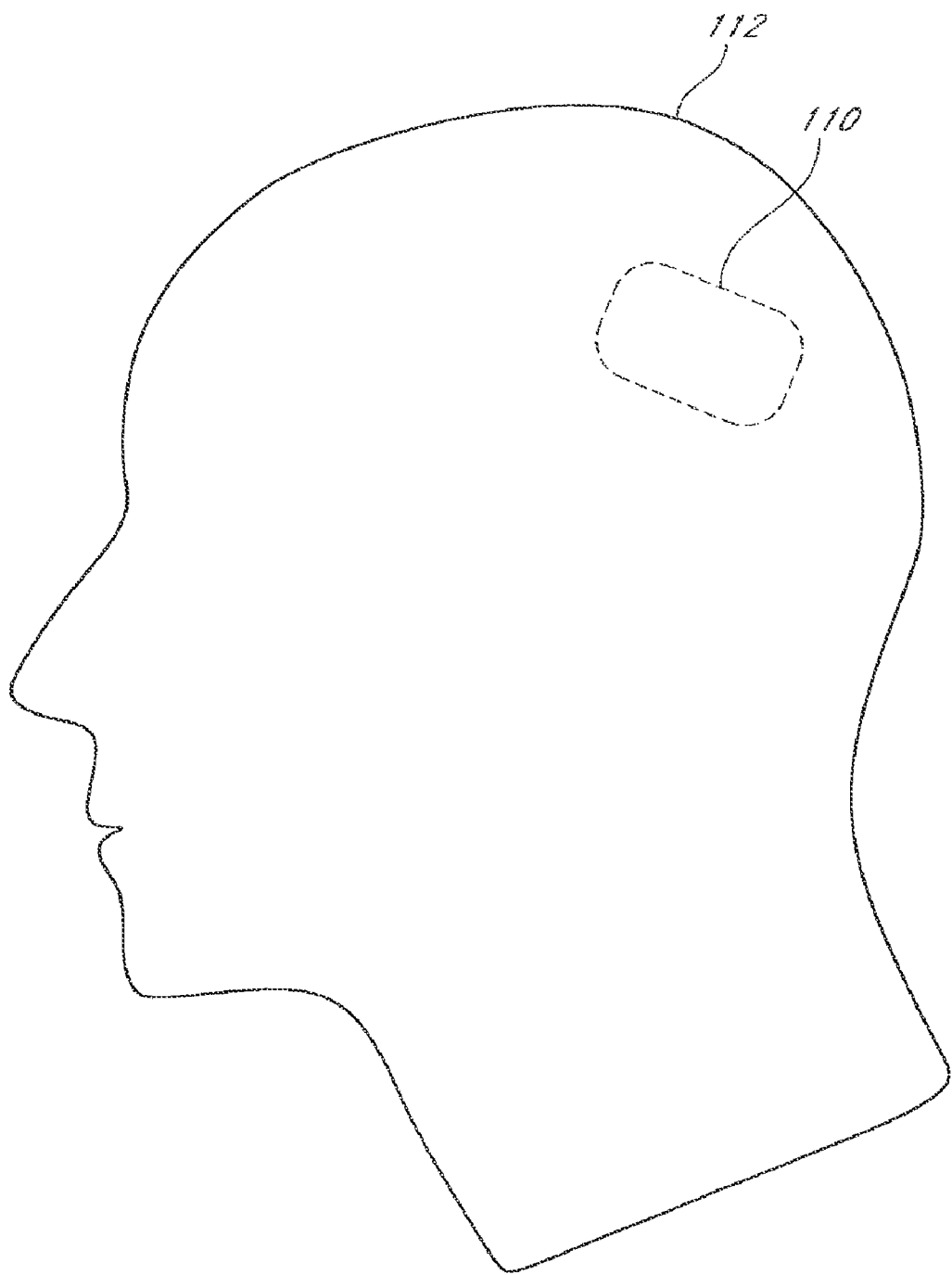
FIG. 1 is a schematic illustration of a patient's head showing the placement of an implantable recording device according to an embodiment.

FIG. 1 depicts an implantable recording device 110 implanted in a patient 112, according to an embodiment. In this embodiment, the implantable recording device 110 comprises a small self-contained brainwave detecting device. As the term is used herein, a brainwave detecting or recording device is a device capable of detecting or predicting ictal activity (or other neurological events) for providing data useful in the diagnosis of a neurological disorder. Further, the term recording device, as used herein, is a device that can either record neurological signals, such as EEG signals, or detect and analyze EEG signals and create a log of such an analysis.

In some embodiments, the implantable recording device 110 is configured to be capable of detecting or predicting any kind of neurological event that has a representative electrographic signature. While the disclosed embodiment is described primarily as responsive to epileptic seizures, it should be recognized that it is also possible to respond to other types of neurological disorders, such as movement disorders (e.g. the tremors characterizing Parkinson's disease), migraine headaches, chronic pain, and neuropsychiatric disorders such as depression. Preferably, neurological events representing any or all of these afflictions can be detected when they are actually occurring, in an onset stage, or as a predictive precursor before clinical symptoms begin.

Figure 2:
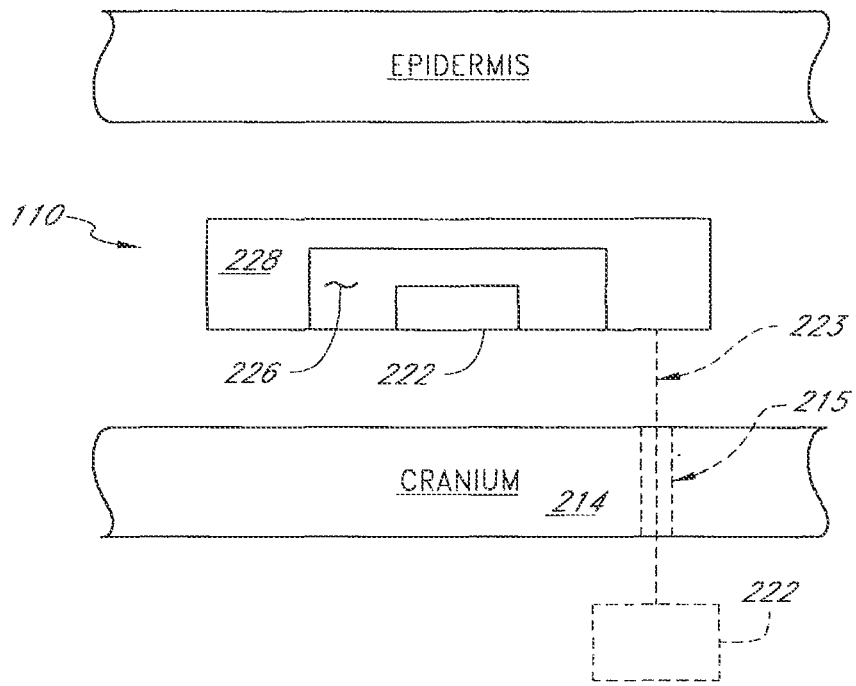
FIG. 2 is a schematic illustration of the placement of the recording device of FIG. 1 between the epidermis and the skull of the patient.

In the disclosed embodiment, the recording device 110 is implanted between a patient's epidermis and skull, for example, as schematically illustrated in FIG. 2. It should be noted, however, that the placement described and illustrated herein is merely exemplary, and other locations and configurations are also possible, depending on the size and shape of the device and individual patient needs, among other factors.

The device 110 is preferably configured to generally follow or to be sufficiently deformable so as to follow the contours of a patient's cranium 214. However, other locations are also possible. For example, the device 110 can be configured to be implanted pectorally (not shown) with leads extending through the patient's neck and between the patient's cranium and epidermis.

It should be recognized that the embodiment of the device 110 described and illustrated herein is preferably a recording device for detecting seizures or their onsets or precursors, and recording or logging these events. For example, the device 110 can be configured to begin recording all or some of the detected EEG signals from the patient at the onset or as a result of a prediction of ictal activity and to continue recording until the ictal activity stops, and optionally, to save such a recording, or a sampling of it, to a memory device for later downloading. Alternatively, or in addition, the device 110 can be configured to create a log of such events.

For example, but without limitation, the device 110 can be configured to record or log the date and time when each such event begins and ends, the duration of the event, indications of the intensity of the event, etc. The device 110 can also be configured, optionally, to download such a log to external equipment, described in greater detail below.

With continued reference to FIG. 2, the device 110 can include housing 226 configured to encapsulate an electronic module that is configured to detect and/or record the desired neurological signals. Additionally, the device 110 can include at least one sensor or sensing electrode 222 configured to be sensitive to electronic neurological signals. For example, but without limitation, the sensor 222 can be formed from a platinum member, or any other type of suitable material. The sensor 222 can be incorporated into the housing 226 or can be connected to the electronics within the housing with a lead implanted in or on the brain or upon the dura at the location of seizure onset so that the device does not need to be located at the seizure onset focus. A separate lead can be used if the seizure onset location was in an area of the brain where the housing could not be implanted due to surgical constraints. A separate lead can also be an option in the event that there are two seizure foci in disparate locations and only one seizure focus would be apparent to a sensor incorporated into the housing.

The device 110 can also include a cushioning member 228 configured to provide a comfortable cushion for the patient. For example, the cushioning member 228 can be comprised of silicone rubber or other types of biocompatible material that can provide a comfortable cushion for a device that is implanted between the epidermis and the cranium 214.

In some embodiments, the housing 226 is suspended completely within the cushioning member 228 such that no portion of the outer surface of the housing 226 is exposed to the outer surface of the cushioning member 228. In other embodiments, the housing 226 can be partially suspended within the cushioning member 228 such that one or more surfaces of the housing 226 are exposed to the outer surface of the cushioning member 228.

In some embodiments, the sensor 222 is exposed to an outer surface of the cushioning member 228 so as to allow the sensor 222 to receive neurological signals from the patient with as little attenuation as possible.

To implant the device 110, firstly, an implantation site is chosen. Because the device 110 can be made quite small, it may be possible to find a cranial contour having a somewhat recessed shape that is also in an acceptable place on the cranium that would serve as an appropriate location for recording ictal brainwaves. A small linear incision can be made at this location with a length that is at least slightly larger than the width of the device. A surgical instrument can be used to elevate the epidermis to form a pocket. In some embodiments, the device 110 can be disposed below the dermis, the subcutaneous tissue, or the galea.

Figure 2A:
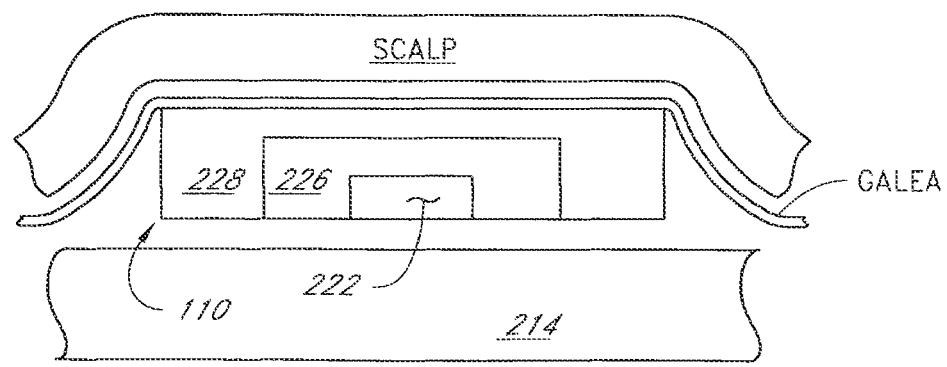
FIG. 2a is a schematic illustration of another optional placement of the recording device of FIG. 1.

For example, as shown in FIG. 2a, the device 110 is illustrated as being disposed beneath the scalp, which comprises the epidermis, dermis, and subcutaneous tissue, and between the galea and the cranium 214. In such an embodiment, the small linear incision is made through the scalp and the galea.

With the epidermis, and/or dermis, and/or subcutaneous tissue, and/or the galea, elevated with a surgical instrument, the device 110 can then be pushed into the space and thus form a pocket around the device 110. For this procedure, local anesthesia can be used and the entire procedure can be completed on the order of 15 minutes. As such, the surgical risks can be reduced.

In some variations, before the device 110 is inserted below the epidermis, dermis, subcutaneous tissue, or galea, an additional recess can be drilled into the cranium 214. For example, a small recess (not shown) can be drilled into the cranium 214 for receiving this sensor 222. As such, the sensor 222 can receive neurological signals with less attenuation because there would be less bone between the sensor 222 and the brain tissue that generates the electrographic activity that is detected. Therefore, the signals would be larger in amplitude which would allow clearer reception for the sensor that would make the detection process easier. And in other alternatives, the craniotomy can be performed where the bone would be completely removed to allow even clearer reception for the sensors 412.

With continued reference to FIG. 2, in yet other alternatives illustrated in phantom, a burr hole 215 can be drilled deeply into the cranium 214 or through the cranium 214. This provides yet clearer reception for the sensor 222. In such alternatives, the sensor 222 can be pressed into such a burr hole, through the cranium 214, and/or into the dura or cortex below the hole. The recess or hole can be sealed after implantation to prevent further movement of the sensor 222 and/or its lead wire 223. For example, U.S. Pat. No. 6,006,124 issued to Fishell et al., which is hereby incorporated by reference as though set forth in full herein, describes such a sealing method.

In other alternatives, the housing 226 can be implanted in an appropriate location of the cranium 214 and a separate lead can be used to connect the electronics within the housing 226 with a sensor 222 implanted in a seizure onset location that is more remote from the location of the housing.

The housing 226 can be fabricated from a biocompatible material. For example, but without limitation, Titanium, which is light, extremely strong, and biocompatible, can be used to form the housing 226.

The housing 226 can enclose a battery and any electronic circuitry, described below in greater detail, to provide the functionality described herein, as well as any other features. As is described in further detail below, a telemetry coil (not shown) can be provided inside or outside of the housing 226 (and potentially integrated with a lead wire connecting the sensor 222 to the housing 226) to facilitate communication between the device 110 and external devices.

The implantable recording device 110 configuration described herein and illustrated in FIGS. 2 and 2a provide several advantages over alternative designs. Firstly, the reduced capabilities of the device 110 allows the entire package to be made much smaller than previous devices that were configured for monitoring and stimulation. This allows the patient to avoid the more risky and expensive craniotomy procedure used for presently available neurostimulator devices. Additionally, the small size of the implantable seizure monitor device 110 causes a minimum of cosmetic disfigurement.

As noted above, and as illustrated in FIG. 3, the recording device 110 can operate in conjunction with external equipment. The device 110 can be mostly autonomous (particularly when performing its usual sensing, detection, and recording capabilities), but preferably includes the selectable part-time wireless link 310 to external equipment, such as a programmer 312.

In the disclosed embodiment, the wireless link 310 can be established by moving a wand (or other apparatus) having communication capabilities and coupled to the programmer 312 into range of the device 110. The programmer 312 can then be used to manually control the operation of the device 110, as well as to transmit information to or receive information from the device 110. Several specific capabilities and operations performed by the programmer 312 in conjunction with the device are described in further detail below.

The programmer 312 can be configured to perform a number of advantageous operations. For example, the programmer 312 can be configured to specify and set variable parameters in the device 110 to adapt the function of the device 110 to meet the patient's needs, download or receive data (including but not limited to stored EEG waveforms, parameters, or logs of events detected) from the device 110 to the programmer 312, upload or transmit program code and other information from the programmer 312 to the device 110, or command the device 110 to perform specific actions or change modes as desired by a physician operating the programmer 312. To facilitate these functions, the programmer 312 is adapted to receive physician input 314 and provide physician output 316; data is transmitted between the programmer 312 and the device 110 over the wireless link 310.

The programmer 312 can be coupled via a communication link 318 to a network 320 such as the Internet. This allows any information downloaded from the device 110, as well as any program code or other information to be uploaded to the device 110, to be stored in a database at one or more data repository locations (which may include various servers and network-connected programmers like the programmer 312). This would allow a patient (and the patient's physician) to have access to important data, including past treatment information and software updates, essentially anywhere in the world that there is a programmer (like the programmer 312) and a network connection.

The device 110 can also have a sensor (not shown) configured to detect a magnetic field. For example, such a sensor can be configured to be triggered by a magnet moved into the vicinity of the device 110 by the patient or caregiver when the patient was experiencing clinical symptoms of a seizure or other significant neurological event. The device 110 can additionally be configured to then store an electrocorticogram sample that would be indicative of the seizure or neurological event. These magnet triggered electrocorticograms could then be analyzed to program the detection parameters.

Figure 4:
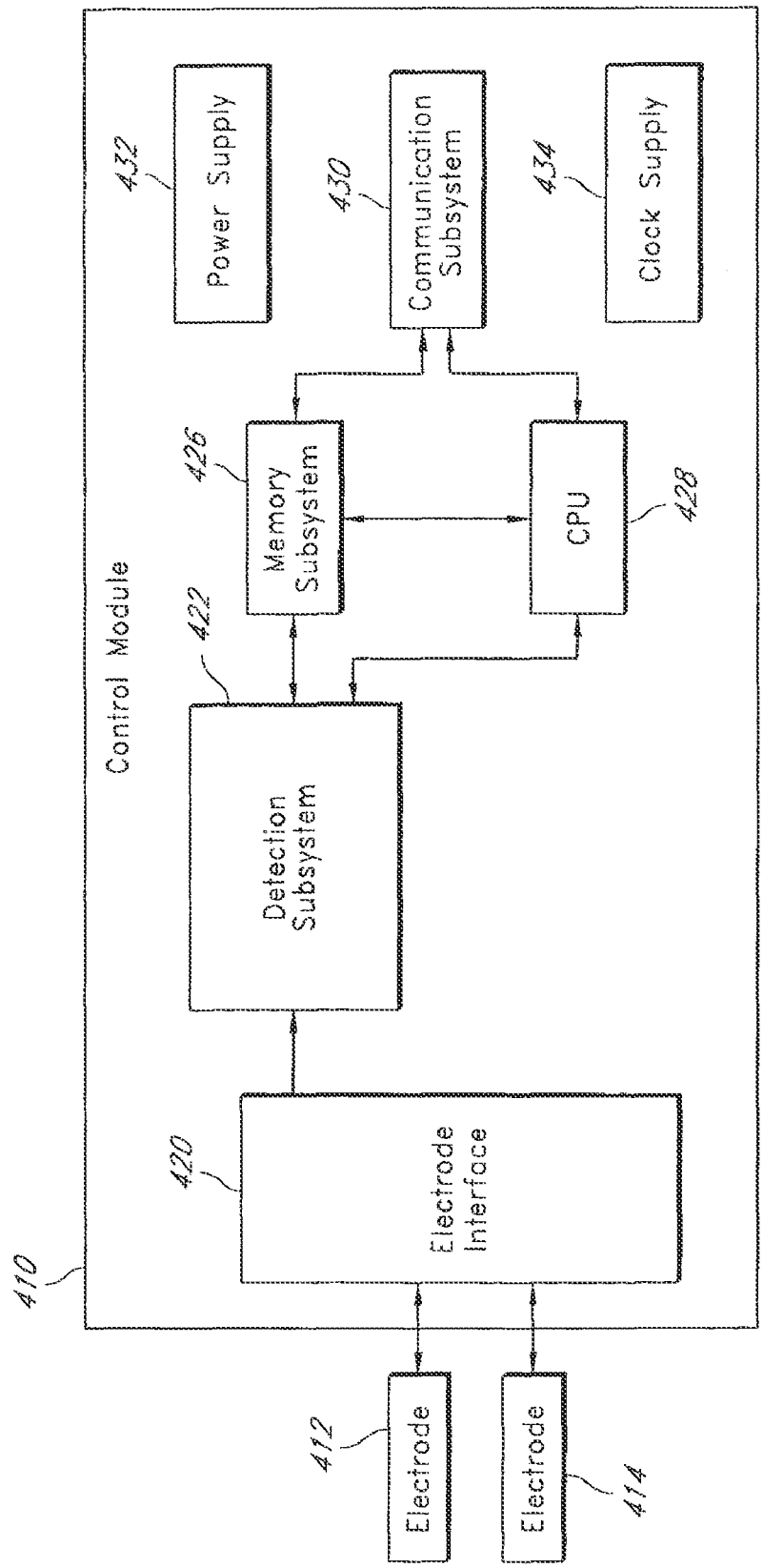
FIG. 4 is a block diagram illustrating the functional subsystems of an implantable recording device according to an embodiment.

An overall block diagram of the device 110 used for measurement, detection, and/or recording is illustrated in FIG. 4. Several subsystems can be disposed within the housing 226 forming a control module 410. The control module can be configured to be coupled to at least one electrode 412. In some embodiments, the control module 410 is configured to be connected to a plurality of electrodes. In some embodiments, the control module 410 is configured to be connected to two electrodes 412, 414, or more electrodes (each of which may be connected to the control module 410 via a lead) for sensing and detection.

The connection between the leads connecting the electrodes 412, 414, to the control module 410 can be accomplished through a lead connector (not shown). Although two electrodes are shown in FIG. 4, it should be recognized that any number is possible. In fact, it is possible to employ an embodiment that uses a single lead with at least two electrodes, or two leads each with a single electrode (or with a second electrode provided by a conductive exterior portion of the housing 226 in one embodiment), although bipolar sensing between two closely spaced electrodes on a lead is preferred to minimize common mode signals including noise.

The electrodes 412, 414 can be connected to an electrode interface 420. Preferably, the electrode interface is capable of selecting each electrode as required for sensing; accordingly the electrode interface is coupled to a detection subsystem 422. The electrode interface can also provide any other features, capabilities, or aspects, including but not limited to amplification, isolation, and charge-balancing functions, that can be used for a proper interface with neurological tissue and not provided by any other subsystem of the device 110.

The detection subsystem 422 can include an EEG analyzer function. The EEG analyzer function can be adapted to receive EEG signals from the electrodes 412, 414, through the electrode interface 420, and to process those EEG signals to identify neurological activity indicative of a seizure, an onset of a seizure, or a precursor to a seizure.

One way to implement such EEG analysis functionality is disclosed in detail in U.S. Pat. No. 6,016,449 to Fischell et al., incorporated by reference above, and additional methods are described in detail below. The detection subsystem can optionally also contain further sensing and detection capabilities, including but not limited to parameters derived from other physiological conditions (such as electrophysiological parameters, temperature, blood pressure, etc.).

The control module 410 can also include a memory subsystem 426 and a central processing unit (CPU) 428, which can take the form of a microcontroller. The memory subsystem can be coupled to the detection subsystem 422 (e.g., for receiving and storing data representative of sensed EEG signals and evoked responses) and the CPU 428, which can control the operation of the memory subsystem 426. In addition to the memory subsystem 426, the CPU 428 can also be connected to the detection subsystem 422 for direct control thereof.

Figure 3:
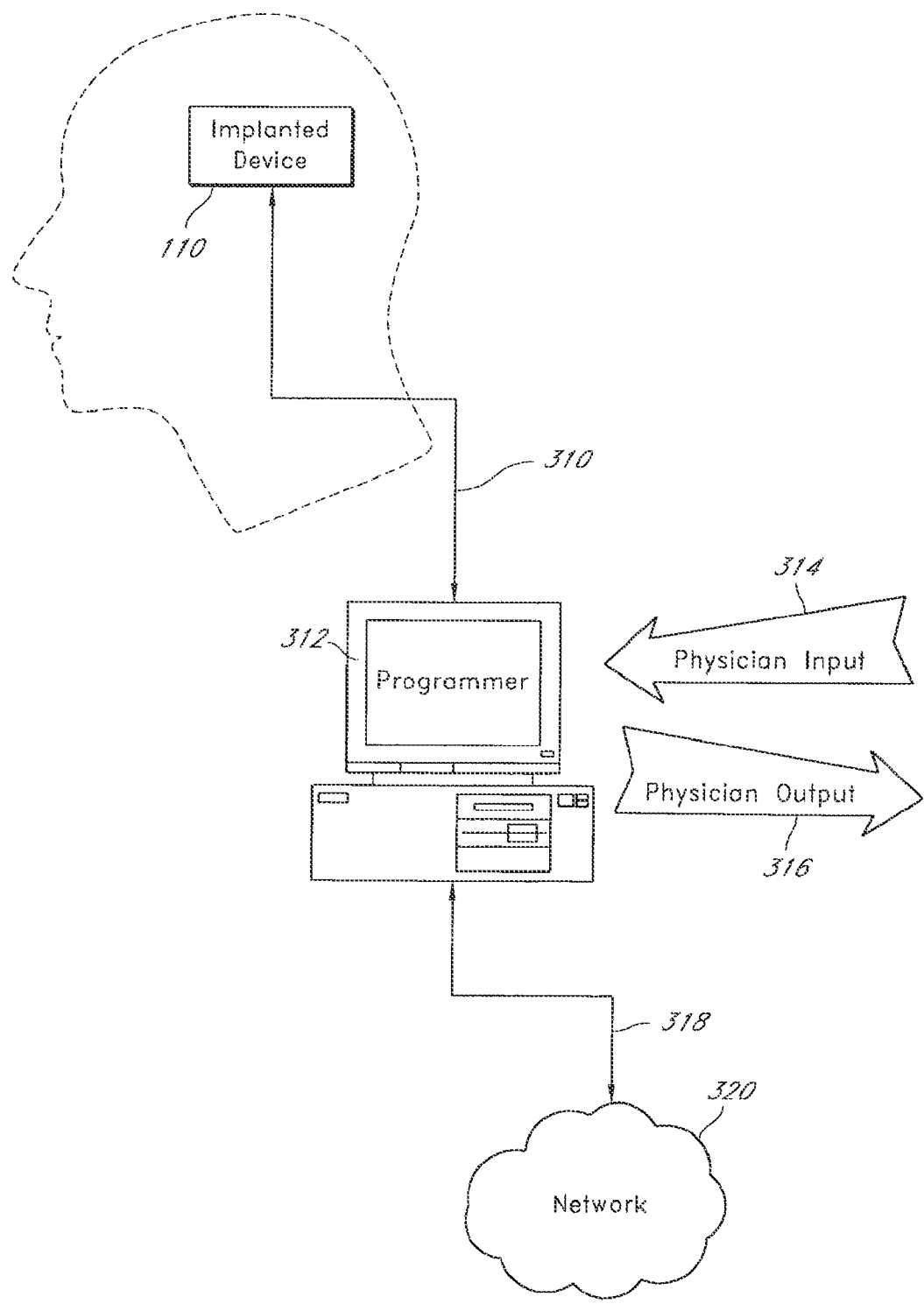
FIG. 3 is a block diagram illustrating an environment of use in which the implantable recording device, in accordance with an embodiment, is implanted and operated.

The control module 410 can also include a communication subsystem 430 which can be coupled to the memory subsystem 426 and the CPU 428. The communication subsystem 430 can be configured to enable communication between the device 110 (FIG. 1) and the outside world, particularly the external programmer 312 (FIG. 3). As noted above, in some embodiments, the communication subsystem 430 can include a telemetry coil (which may be situated outside of the housing 226) enabling transmission and reception of signals, to or from an external apparatus, via inductive coupling. Alternative embodiments of the communication subsystem 430 could use an antenna for an RF link or an audio transducer for an audio link to the patient to provide indications of neurological events or system status, or other indications.

The control module 410 can include other subsystems. For example, the control module 410 can include a power supply 432 and a clock supply 434. The power supply 432 can be configured to supply the voltages and currents desired for each of the other subsystems. The clock supply 434 can be configured to supply substantially all of the other subsystems with any clock and/or timing signals desired for their operation.

It should be noted that while the memory subsystem 426 is illustrated in FIG. 4 as a separate functional subsystem, the other subsystems can also be configured to use various amounts of memory to perform the functions described herein, as well as other functions. Furthermore, while the control module 410 is preferably a single physical unit contained within a single physical enclosure, namely the housing 226 (FIG. 2), it can comprise a plurality of spacially separate units each performing a subset of the capabilities described above. Also, it should be noted that the various functions and capabilities of the subsystems described herein can be performed by electronic hardware (e.g., hard wired modules), computer software (or firmware), or a combination thereof. The division of work between the CPU 428 and other functional subsystems can also vary—the functional distinctions illustrated in FIG. 4 may not reflect the integration of functions in a real-world system or method according to the embodiments disclosed herein.

Rounding out the subsystems in the control module 410 are a power supply 432 and a clock supply 434. The power supply 432 supplies the voltages and currents necessary for each of the other subsystems. The clock supply 434 supplies substantially all of the other subsystems with any clock and timing signals necessary for their operation.

Figure 5:
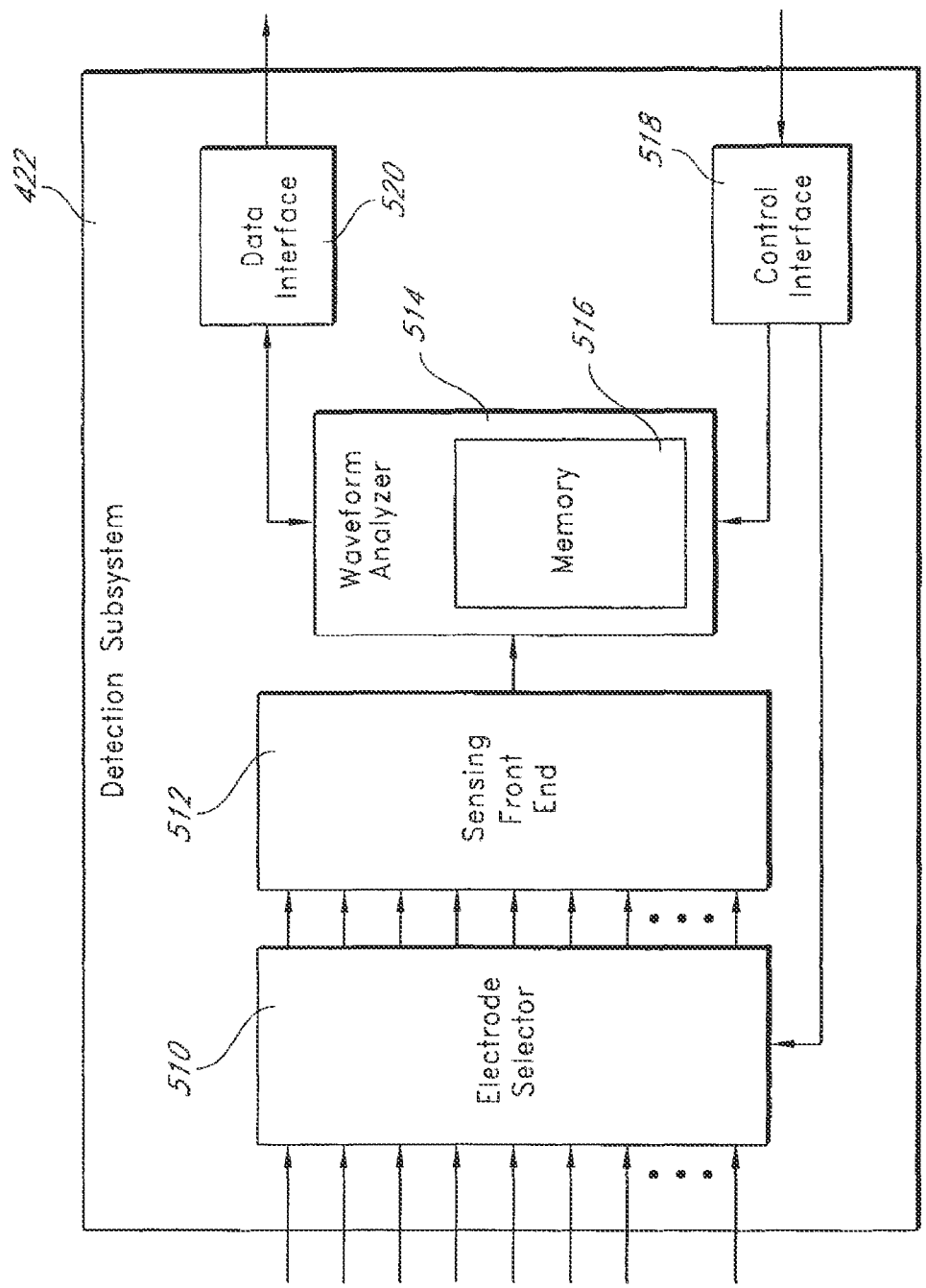
FIG. 5 is a block diagram illustrating the functional components of the detection subsystem of the implantable recording device shown in FIG. 4.

FIG. 5 illustrates details of the detection subsystem 422 (FIG. 4). Inputs from the electrodes 412, 414 are on the left, and connections to other subsystems are on the right.

Signals received from the electrodes 412, 414 (as routed through the electrode interface 420) are received in an electrode selector 510. The electrode selector 510 allows the device to select which electrodes should be routed to which individual sensing channels of the detection subsystem 422, based on commands received through a control interface 518 from the memory subsystem 426 or the CPU 428 (FIG. 4).

Preferably, each sensing channel of the detection subsystem 422 receives a bipolar signal representative of the difference in electrical potential between two selectable electrodes. Accordingly, the electrode selector 510 provides signals corresponding to each pair of selected electrodes to a sensing front end 512, which performs amplification, analog to digital conversion, and multiplexing functions on the signals in the sensing channels. The sensing front end is described further below in connection with FIG. 6. In some embodiments, where the device 110 only includes two sensors (e.g., sensors 412, 414), the electrode selector 510 can be eliminated, allowing the detection subsystem 422 to operate only on a single channel. This provides an advantage of further reducing the size of the overall device 110.

A multiplexed input signal representative of all active sensing channels can then be fed from the sensing front end 512 to a waveform analyzer 514. The waveform analyzer 514 is preferably a special-purpose digital signal processor (DSP) adapted for use with the embodiment, or in an alternative embodiment, can comprise a programmable general-purpose DSP.

In some embodiments, the waveform analyzer can have its own scratchpad memory area 516 used for local storage of data and program variables when signal processing is being performed. In either case, the signal processor performs suitable measurement and detection methods described generally above and in greater detail below. Any results from such methods, as well as any digitized signals intended for storage transmission to external equipment, are passed to various other subsystems of the control module 410, including the memory subsystem 426 and the CPU 428 (FIG. 4) through a data interface 520. Similarly, the control interface 518 allows the waveform analyzer 514 and the electrode selector 510 to be in communication with the CPU 428.

Figure 6:
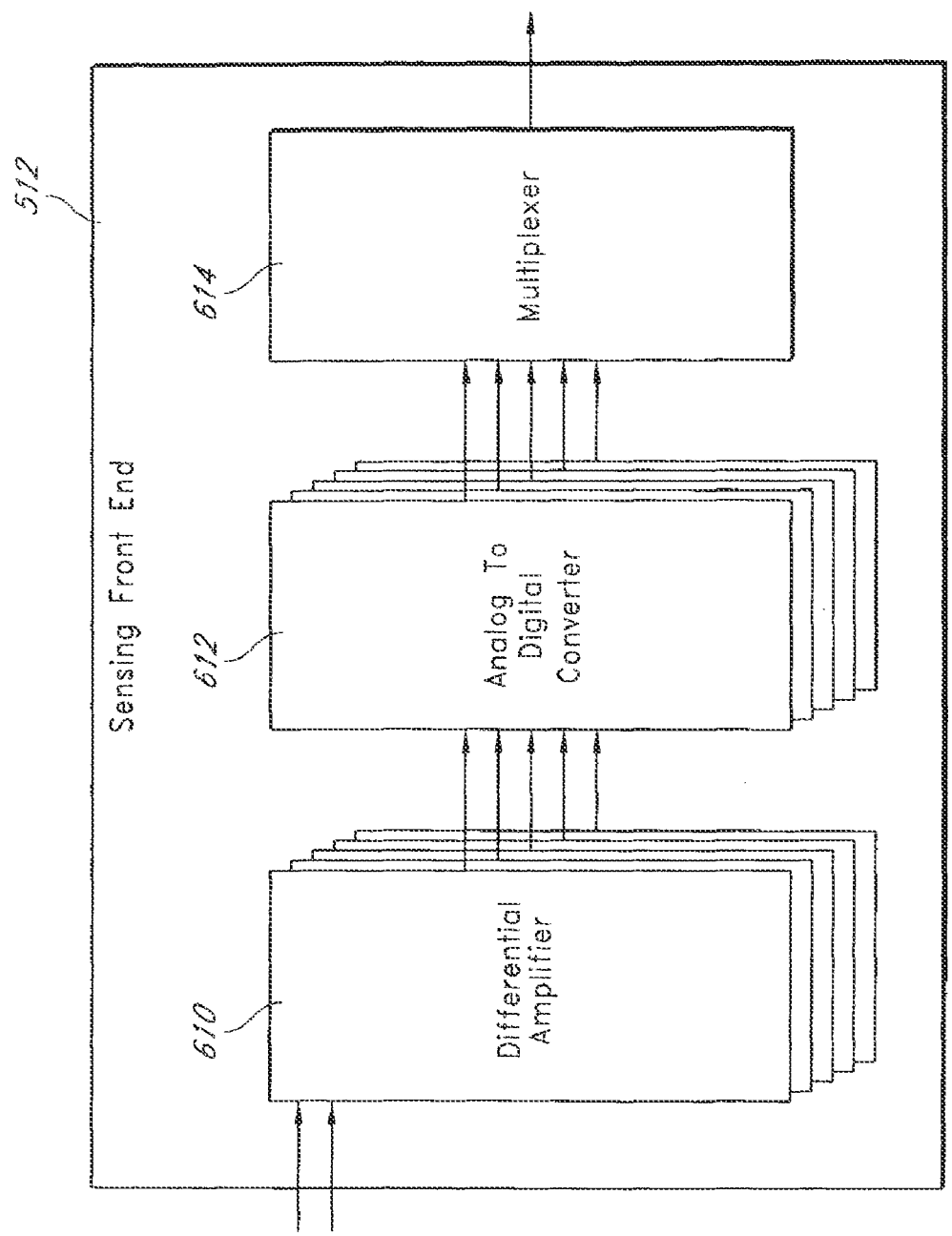
FIG. 6 is a block diagram illustrating the functional components of the sensing front end of the detection subsystem of FIG. 5.

With reference to FIG. 6, the sensing front end 512 (FIG. 5) is illustrated in further detail. As shown, the sensing front end includes a plurality of differential amplifier channels 610, each of which receives a selected pair of inputs from the electrode selector 510.

In some embodiments, each of the differential amplifier channels 610 is adapted to receive or to share inputs with one or more other differential amplifier channels 610 without adversely affecting the sensing and detection capabilities of a system according to some embodiments. For clarity, only one channel is illustrated in FIG. 6, but it should be noted that any practical number of sensing channels may be employed in a system according to some embodiments.

Each differential amplifier channel 610 feeds a corresponding analog to digital converter (ADC) 612. Preferably, the analog to digital converters 612 are separately programmable with respect to sample rates—in the disclosed embodiment, the ADCs 612 convert analog signals into 10-bit unsigned integer digital data streams at a sample rate selectable between 250 Hz and 500 Hz.

In several of the illustrations described below where waveforms are shown, sample rates of 250 Hz are typically used for simplicity. However, the inventions disclosed herein shall not be deemed to be so limited, and numerous sample rate and resolution options are possible, with tradeoffs known to individuals of ordinary skill in the art of electronic signal processing. The resulting digital signals are received by a multiplexer 614 that creates a single interleaved digital data stream representative of the data from all active sensing channels. As described in further detail below, not all of the sensing channels need to be used at one time, and it may in fact be advantageous in certain circumstances to deactivate certain sensing channels to reduce the power consumed by a system according to some embodiments.

It should be noted that as illustrated and described herein, a "sensing channel" is not necessarily a single physical or functional item that can be identified in any illustration. Rather, a sensing channel can be formed from the functional sequence of operations described herein, and particularly represents a single electrical signal received from any pair or combination of electrodes, as preprocessed by a system according to some embodiments, in both analog and digital forms. See, e.g., U.S. patent application Ser. No. 09/517,797 to D. Fischell et al., filed on Mar. 2, 2000 and entitled "Neurological Event Detection Using Processed Display Channel Based Algorithms and Devices Incorporating These Procedures," which is hereby incorporated by reference as though set forth in full herein. At times (particularly after the multiplexer 614), multiple sensing channels are processed by the same physical and functional components of the system; notwithstanding that, it should be recognized that unless the description herein indicates to the contrary, a system according to some embodiments processes, handles, and treats each sensing channel independently.

The interleaved digital data stream is passed from the multiplexer 614, out of the sensing front end 512, and into the waveform analyzer 514. The waveform analyzer 514 is illustrated in detail in FIG. 7.

The interleaved digital data stream representing information from all of the active sensing channels is first received by a channel controller 710. The channel controller applies information from the active sensing channels to a number of wave morphology analysis units 712 and window analysis units 714. It is preferred to have as many wave morphology analysis units 712 and window analysis units 714 as possible, consistent with the goals of efficiency, size, and low power consumption necessary for an implantable device. In some embodiments, there are sixteen wave morphology analysis units 712 and eight window analysis units 714, each of which can receive data from any of the sensing channels of the sensing front end 512, and each of which can be operated with different and independent parameters, including differing sample rates, as will be discussed in further detail below.

Further, in some embodiments, such as embodiments using only a single bipole channel, the wave form analyzer 514 can operate with as little as one or two wave morphology analysis units 712 and one or two window analysis units 714, each of which can receive data from the single channel of the sensing front end 512, each of which can be operated with different and independent parameters, including different sampling rates. Reducing the number of wave morphology analysis units 712 and window analysis units 714 allows the recording device 110 to be further reduced in size.

Each of the wave morphology analysis units 712 can operate to extract certain feature information from an input waveform as described below in conjunction with FIGS. 9-11. Similarly, each of the window analysis units 714 can perform certain data reduction and signal analysis within time windows in the manner described in conjunction with FIGS. 12-17. Output data from the various wave morphology analysis units 712 and window analysis units 714 can be combined via event detector logic 716. The event detector logic 716 and the channel controller 710 can be controlled by control commands 718 received from the control interface 518 (FIG. 5).

A "detection channel," as the term is used herein, refers to a data stream including the active sensing front end 512 and the analysis units of the waveform analyzer 514 processing that data stream, in both analog and digital forms. It should be noted that each detection channel can receive data from a single sensing channel; each sensing channel preferably can be applied to the input of any combination of detection channels. The latter selection is accomplished by the channel controller 710. As with the sensing channels, not all detection channels need to be active; certain detection channels can be deactivated to save power or if additional detection processing is deemed unnecessary in certain applications.

In conjunction with the operation of the wave morphology analysis units 712 and the window analysis units 714, a scratchpad memory area 516 can be provided for temporary storage of processed data. The scratchpad memory area 516 can be physically part of the memory subsystem 426, or alternatively may be provided for the exclusive use of the waveform analyzer 514. Other subsystems and components of a system according to an embodiment can also be furnished with local scratchpad memory, if such a configuration is desired.

Figure 8:
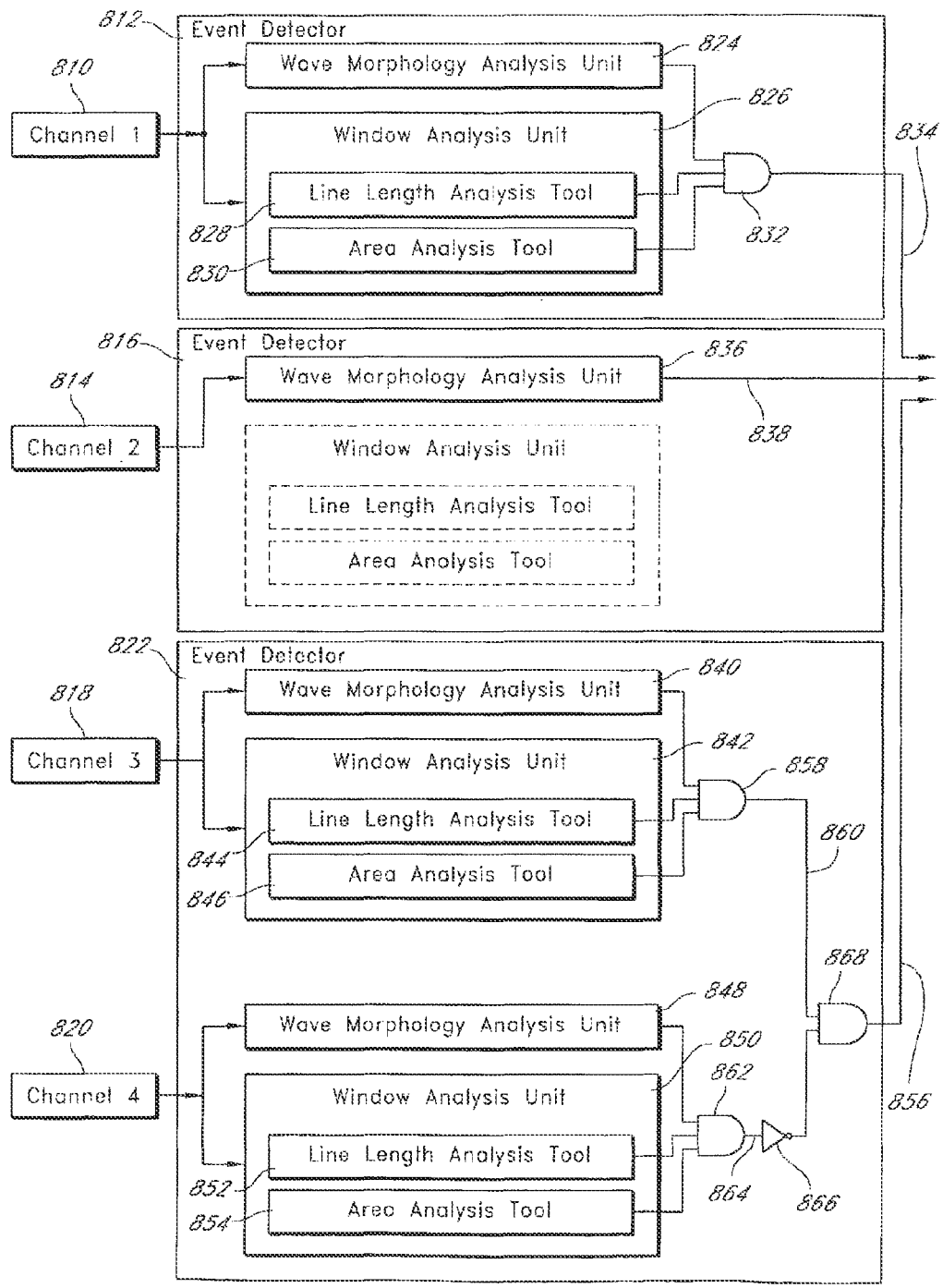
FIG. 8 is a block diagram illustrating the functional arrangement of components of the waveform analysis of the detection subsystem of FIG. 5 in a possible programmed embodiment.

An exemplary but non-limiting operation of the event detector logic 716 is illustrated in detail in the functional block diagram of FIG. 8, in which four exemplary sensing channels are analyzed by three illustrative event detectors.

A first sensing channel 810 provides input to a first event detector 812. While the first event detector 812 is illustrated as a functional block in the block diagram of FIG. 8, it should be recognized that it is a functional block only for purposes of illustration, and may not have any physical counterpart in a device according to some embodiments. Similarly, a second sensing channel 814 provides input to a second event detector 816, and a third input channel 818 and a fourth input channel 820 both provide input to a third event detector 822. Additionally, in embodiments using only a single channel, either one of the event detectors 812, 816, described below in greater detail, can be used. However, other configurations can also be used.

Figure 7:
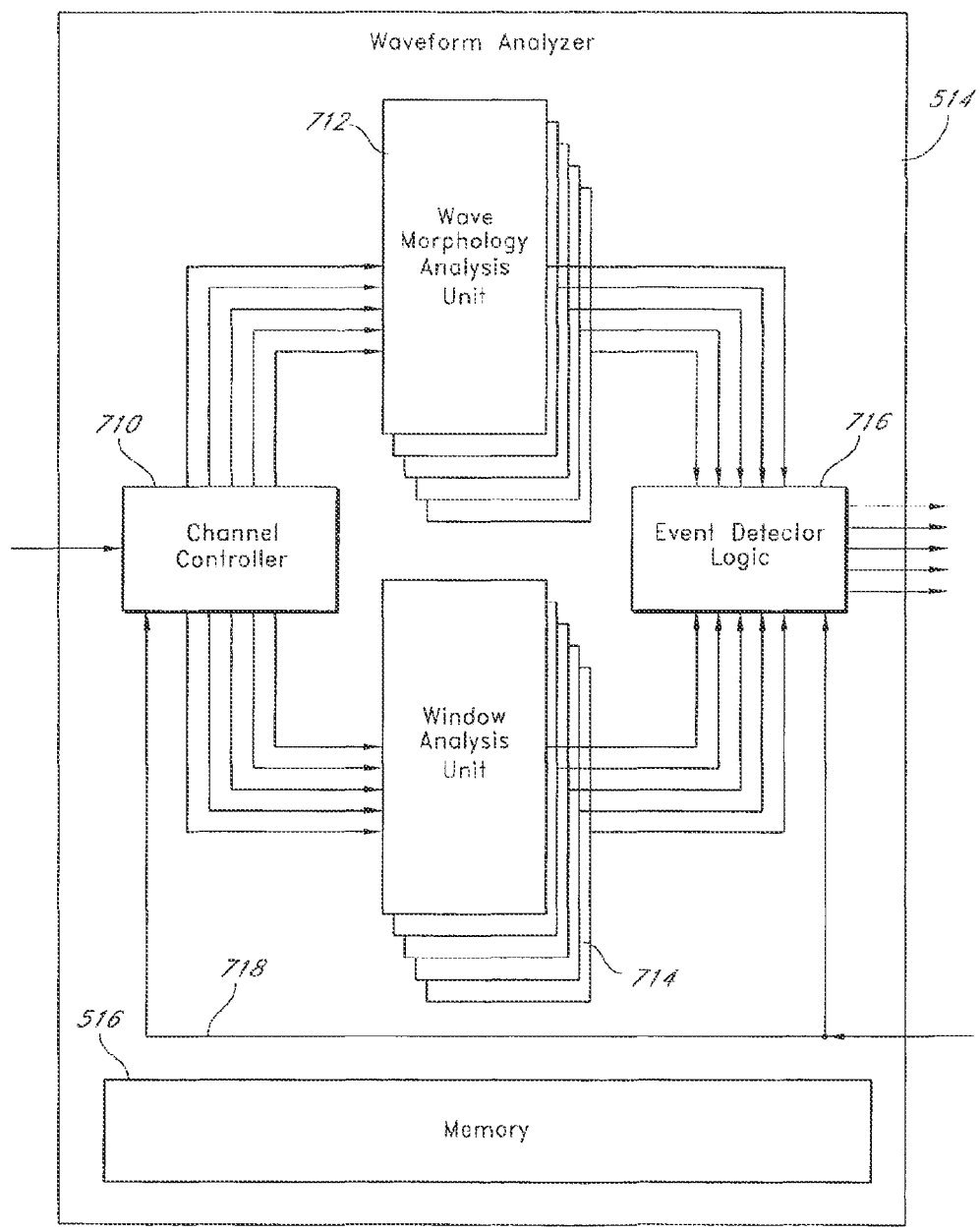
FIG. 7 is a block diagram illustrating the components of the waveform analyzer of the detection subsystem of FIG. 5.

Considering the processing performed by the event detectors 812, 816, and 822, the first input channel 810 feeds a signal to both a wave morphology analysis unit 824 (one of the wave morphology analysis units 712 of FIG. 7) and a window analysis unit 826 (one of the window analysis units 714 of FIG. 7). The window analysis unit 826, in turn, includes a line length analysis tool 828 and an area analysis tool 830. As discussed in detail below, the line length analysis tool 828 and the area analysis tool 830 can be configured to analyze different aspects of the signal from the first input channel 810.

Outputs from the wave morphology analysis unit 824, the line length analysis tool 828, and the area analysis tool 830 can be combined in a Boolean AND operation 832 and sent to an output 834 for further use by a system according to an embodiment. For example, if a combination of analysis tools in an event detector identifies several simultaneous (or near-simultaneous) types of activity in an input channel, a system according to an embodiment can be programmed to perform an action in response thereto. Exemplary details of the analysis tools and the combination processes that can be used in the event detectors are described in greater detail below.

In the second event detector 816, only a wave morphology analysis unit 836 is active. Accordingly, no Boolean operation needs to be performed, and the wave morphology analysis unit 836 directly feeds an event detector output 838.

The third event detector 822 can operate on two input channels 818 and 820, and can include two separate detection channels of analysis units: a first wave morphology analysis unit 840 and a first window analysis unit 842, the latter including a first line length analysis tool 844 and a first area analysis tool 846; and a second wave morphology analysis unit 848 and a second window analysis unit 850, the latter including a second line length analysis tool 852 and a second area analysis tool 854. The two detection channels of analysis units can be combined to provide a single event detector output 856.

In the first detection channel of analysis units 840 and 842, outputs from the first wave morphology analysis unit 840, the first line length analysis tool 844, and the first area analysis tool 846 can be combined via a Boolean AND operation 858 into a first detection channel output 860. Similarly, in the second detection channel of analysis units 848 and 850, outputs from the second wave morphology analysis unit 848, the second line length analysis tool 852, and the second area analysis tool 854 can be combined via a Boolean AND operation 862 into a second detection channel output 864. In the illustrated embodiment, the second detection channel output 864 is invertible with selectable Boolean logic inversion 866 before it is combined with the first detection channel output 860. Subsequently, the first detection channel output 860 and the second detection channel output 864 are combined with a Boolean AND operation 868 to provide a signal to the output 856. In an alternative embodiment, a Boolean OR operation is used to combine the first detection channel output 860 and the second detection channel output 864.

In some embodiments, the second detection channel (analysis units 848 and 850) represents a "qualifying channel" with respect to the first detection channel (analysis units 840 and 842). In general, a qualifying channel allows a detection to be made only when both channels are in concurrence with regard to detection of an event. For example, a qualifying channel can be used to indicate when a seizure has "generalized," i.e. spread through a significant portion of a patient's brain. To do this, the third input channel 818 and the fourth input channel 820 can be configured to receive EEG waveforms from separate amplifier channels coupled to electrodes in separate parts of the patient's brain (e.g., in opposite hemispheres). Accordingly, then, the Boolean AND operation 868 will indicate a detection only when the first detection output 860 and the second detection output 864 both indicate the presence of an event (or, when Boolean logic inversion 866 is present, when the first detection output 860 indicates the presence of an event while the second detection output 864 does not). As described in further detail below, the detection outputs 860 and 864 can be provided with selectable persistence (i.e., the ability to remain triggered for some time after the event is detected), allowing the Boolean AND combination 868 to be satisfied even when there is not precise temporal synchronization between detections on the two channels.

It should be appreciated that the concept of a "qualifying channel" allows the flexible configuration of a device 110 to achieve a number of advantageous results. In addition to the detection of generalization, as described above, a qualifying channel can be configured, for example, to detect noise so a detection output is valid only when noise is not present, to assist in device configuration in determining which of two sets of detection parameters is preferable (by setting up the different parameters in the first detection channel and the second detection channel, then replacing the Boolean AND combination with a Boolean OR combination), or to require a specific temporal sequence of detections (which would be achieved in software by the CPU 428 after a Boolean OR combination of detections). There are numerous other possibilities.

The outputs 834, 838, and 856 of the event detectors are preferably represented by Boolean flags, and as described below, provide information for the operation of a system according to an embodiment.

While FIG. 8 illustrates four different sensing channels providing input to four separate detection channels, it should be noted that maximally flexible embodiments would allow each sensing channel to be connected to one or more detection channels. It can be advantageous to program the different detection channels with different settings (e.g., thresholds) to facilitate alternate "views" of the same sensing channel data stream.

Figure 9:
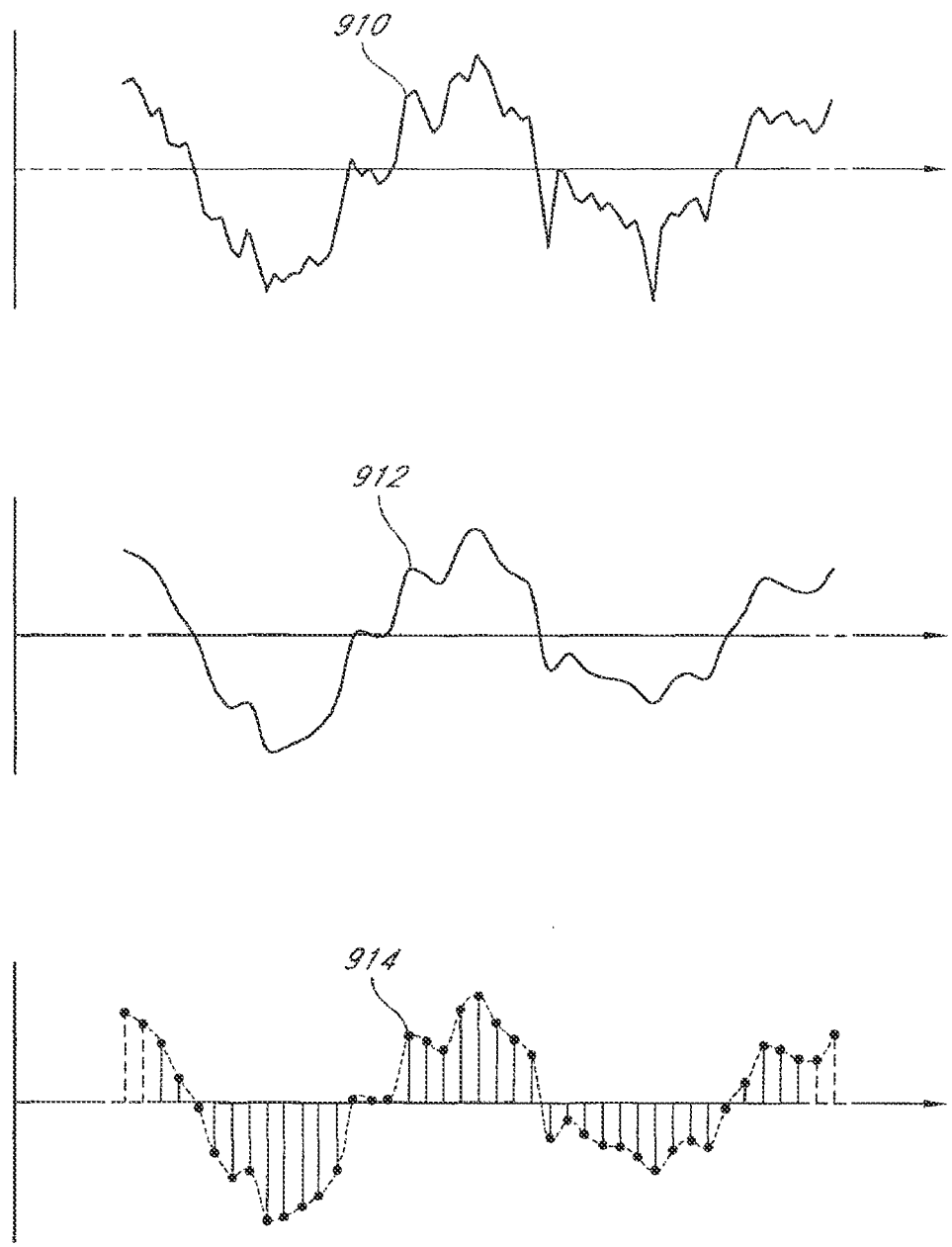
FIG. 9 is a graph of an exemplary EEG signal, illustrating decomposition of the signal into time windows and samples.

FIG. 9 illustrates three representative waveforms of the type expected to be manipulated by a system according to some embodiments. It should be noted, however, that the waveforms illustrated in FIG. 9 are illustrative only, and are not intended to represent any actual data. The first waveform 910 is representative of an unprocessed electroencephalogram (EEG) or electrocorticogram (ECOG) waveform having a substantial amount of variability; the illustrated segment has a duration of approximately 160 ms and a dominant frequency (visible as the large-scale crests and valleys) of approximately 12.5 Hz. It will be recognized that the first waveform is rather rough and peaky; there is a substantial amount of high-frequency energy represented therein.

The second waveform 912 represents a filtered version of the original EEG waveform 910. As shown, most of the high-frequency energy has been eliminated from the signal, and the waveform 912 is significantly smoother. In the disclosed embodiment, this filtering operation is performed in the sensing front end 512 before the analog to digital converters 612 (FIG. 6).

The filtered waveform 912 can then be sampled by one of the analog to digital converters 612; this operation is represented graphically in the third waveform 914 of FIG. 9. As illustrated, a sample rate used in some embodiments is 250 Hz (4 ms sample duration), resulting in approximately 40 samples over the illustrated 160 ms segment. As is well known in the art of digital signal processing, the amplitude resolution of each sample is limited; in some embodiments, each sample is measured with a resolution of 10 bits (or 1024 possible values). As is apparent upon visual analysis of the third waveform, the dominant frequency component has a wavelength of approximately 20 samples, which corresponds to the dominant frequency of 12.5 Hz.

Figure 10:
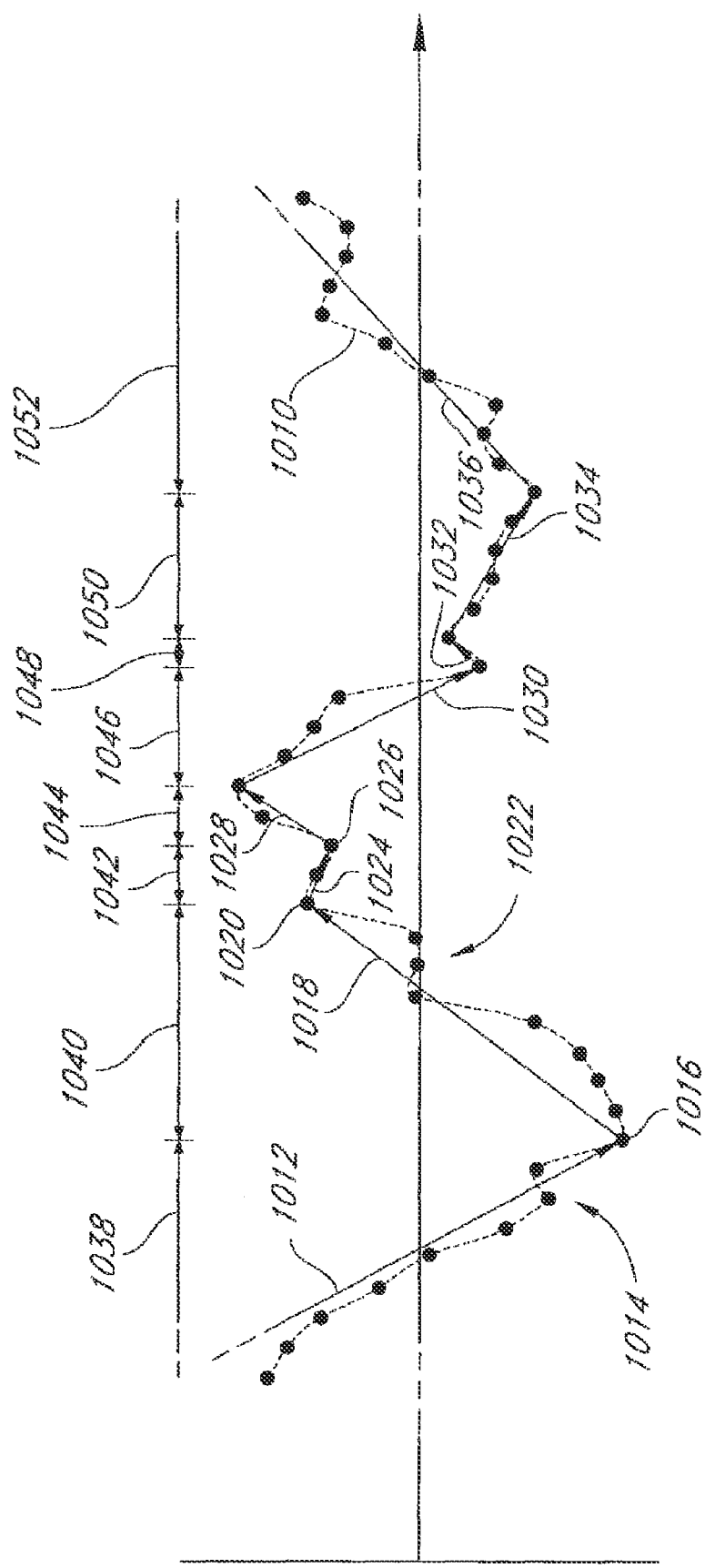
FIG. 10 is a graph of the exemplary EEG signal of FIG. 9, illustrating the extraction of half waves from the signal.

Referring now to FIG. 10, the processing of the wave morphology analysis units 712 is described in conjunction with a filtered and sampled waveform 1010 of the type illustrated as the third waveform 914 of FIG. 9.

In a first half wave 1012, which is partially illustrated in FIG. 10 (the starting point occurs before the illustrated waveform segment 1010 begins), the waveform segment 1010 is essentially monotonically decreasing, except for a small first perturbation 1014. Accordingly, the first half wave 1012 is represented by a vector from the starting point (not shown) to a first local extremum 1016, where the waveform starts to move in the opposite direction. The first perturbation 1014 is of insufficient amplitude to be considered a local extremum, and is disregarded by a hysteresis mechanism (discussed in further detail below).

A second half wave 1018 extends between the first local extremum 1016 and a second local extremum 1020. Again, a second perturbation 1022 is of insufficient amplitude to be considered an extremum. Likewise, a third half wave 1024 extends between the second local extremum 1020 and a third local extremum 1026; this may appear to be a small perturbation, but is greater in amplitude than a selected hysteresis threshold. The remaining half waves 1028, 1030, 1032, 1034, and 1036 are identified analogously. As will be discussed in further detail below, each of the identified half waves 1012, 1018, 1024, 1028, 1030, 1032, 1034, and 1036 has a corresponding duration 1038, 1040, 1042, 1044, 1046, 1048, 1050, and 1052, respectively, and analogously, a corresponding amplitude determined from the relative positions of each half wave's starting point and ending point along the vertical axis, and a slope direction, increasing or decreasing.

In a method performed according to some embodiments, it is particularly advantageous to allow for a programmable hysteresis setting in identifying the ends of half waves. In other words, as explained above, the end of an increasing or decreasing half wave might be prematurely identified as a result of quantization (and other) noise, low-amplitude signal components, and other perturbing factors, unless a small hysteresis allowance is made before a reversal of waveform direction (and a corresponding half wave end) is identified. Hysteresis allows for insignificant variations in signal level inconsistent with the signal's overall movement to be ignored without the need for extensive further signal processing such as filtering. Without hysteresis, such small and insignificant variations might lead to substantial and gross changes in where half waves are identified, leading to unpredictable results.

Figure 11:
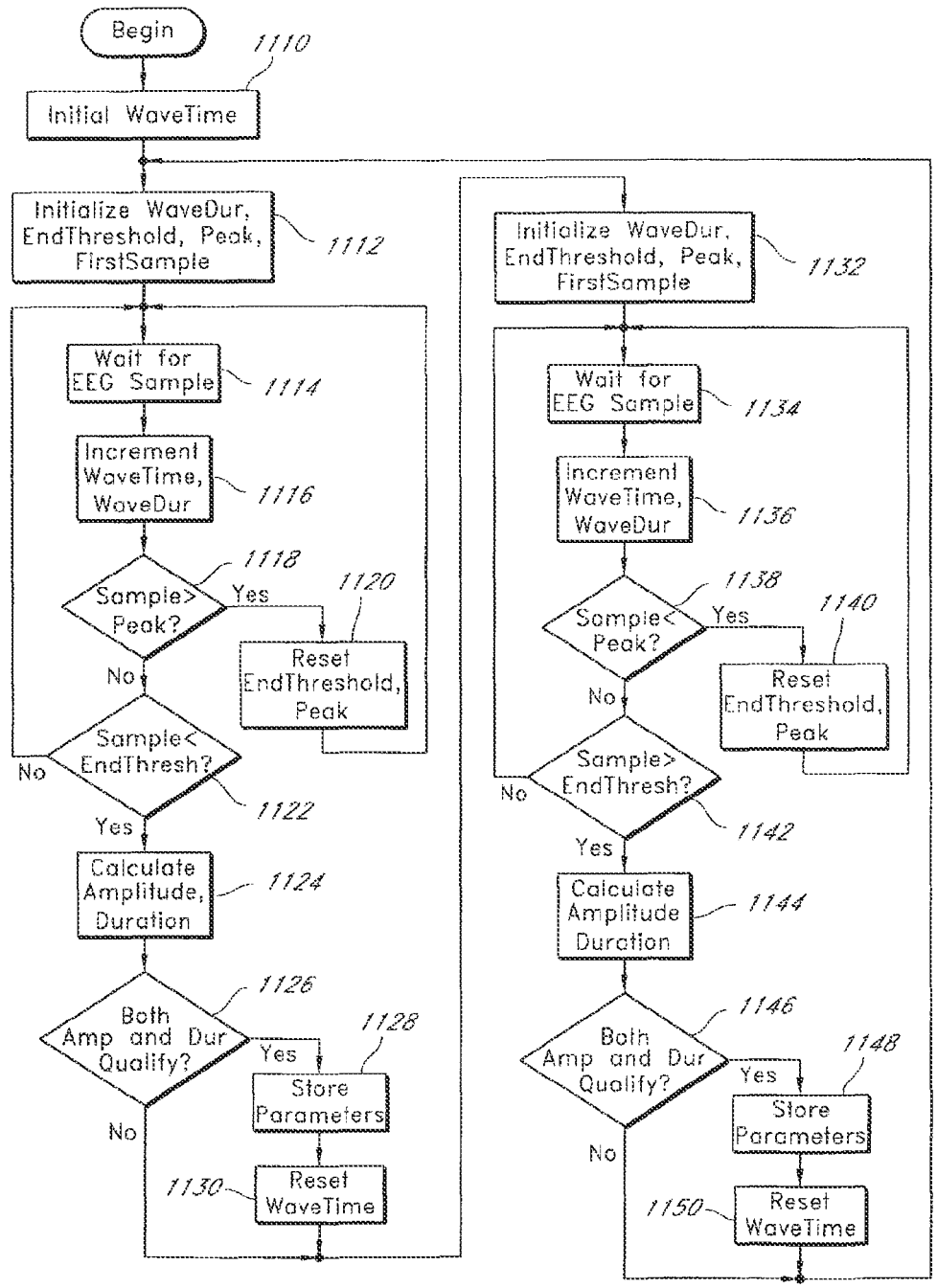
FIG. 11 is a flow chart illustrating the process performed by hardware functional components of the waveform analyzer of FIG. 7 in extracting half waves as illustrated in FIG. 10.

The processing steps performed with regard to the waveform 1010 and half waves of FIG. 10 are set forth in FIG. 11. The method begins by identifying an increasing half wave (with an ending amplitude higher than the starting amplitude, as in the second half wave 1018 of FIG. 10). To do this, a variable corresponding to half wave time is first initialized to zero (step 1110); then half wave duration, ending threshold, peak amplitude, and first sample value are all initialized (step 1112). Specifically, the half wave duration value is set to zero; the peak amplitude and first sample values are set to the amplitude value of the last observed sample, which as described above is a value having 10-bit precision; and the ending threshold is set to the last observed sample minus a small preset hysteresis value. After waiting for a measurement of the current EEG sample (step 1114), the half wave time and half wave duration variables are incremented (step 1116). If the current EEG sample has an amplitude greater than the peak amplitude (step 1118), then the amplitude of the half wave is increasing (or continues to increase). Accordingly, the ending threshold is reset to be the current EEG sample's amplitude minus the hysteresis value, and the peak is reset to the current EEG sample's amplitude (step 1120), and the next sample is awaited (step 1114).

If the current EEG sample has an amplitude less than the ending threshold (step 1122), then the hysteresis value has been exceeded, and a local extremum has been identified. Accordingly, the end of the increasing half wave has been reached, and the amplitude and duration of the half wave are calculated (step 1124). The amplitude is equal to the peak amplitude minus the first sample value; the duration is equal to the current half wave duration. Otherwise, the next ample is awaited (step 1114).

If both the amplitude and the duration qualify by exceeding corresponding preset thresholds (step 1126), then the amplitude, duration, half wave time, half wave direction (increasing) are stored in a buffer (step 1128), and the half wave time is reset to zero (step 1130).

At the conclusion of the increasing half wave, the process continues by initializing wave duration, the ending threshold, the peak amplitude, and the first sample value (step 1132). Wave duration is set to zero, the ending threshold is set to the last sample value plus the hysteresis value, the peak amplitude and the first sample value are set to the most recent sample value.

After waiting for a measurement of the current EEG sample (step 1134), the half wave time and half wave duration variables are incremented (step 1136). If the current EEG sample has an amplitude lower than the peak amplitude (step 1138), then the amplitude of the half wave is decreasing (or continues to decrease). Accordingly, the ending threshold is reset to be the current EEG sample's amplitude plus the hysteresis value, the peak is reset to the current EEG sample's amplitude (step 1140), and the next sample is awaited (step 1134).

If the current EEG sample has an amplitude greater than the ending threshold (step 1142), then the hysteresis value has been exceeded, and a local extremum has been identified. Accordingly, the end of the decreasing half wave has been reached, and the amplitude and duration of the half wave are calculated (step 1144). The amplitude is equal to the first sample value minus the peak amplitude, and the duration is equal to the current half wave duration. Otherwise, the next EEG sample is awaited (step 1134).

If both the amplitude and the duration qualify by exceeding corresponding preset thresholds (step 1146), then the amplitude, duration, half wave time, half wave direction (decreasing) are stored in a buffer (step 1148), and the half wave time is reset to zero (step 1150). It should be noted that, in the context of this specification, the term "exceed" in regard to a threshold value means to meet a specified criterion. Generally, to exceed a threshold herein is to have a numeric value greater than or equal to the threshold, although other interpretations (such as greater than, or less than, or less than or equal to, depending on the context) may be applicable and are deemed to be within the scope of the present inventions.

At the conclusion of the decreasing half wave, further half waves are then identified by repeating the process from step 1112. As half wave detection is an ongoing and continuous process, this procedure preferably does not exit, but may be suspended from time to time when conditions or device state call for it, e.g. when the device is inactive. Once suspended, the procedure should recommence with the first initialization step 1110.

Accordingly, the process depicted in FIG. 11 stores parameters corresponding to qualified half waves, including their directions, durations, amplitudes, and the elapsed time between adjacent qualified half waves (i.e. the half wave time variable). In some embodiments, to reduce power consumption, this procedure is performed in custom electronic hardware; it should be clear that the operations of FIG. 11 can be performed in parallel for each active instance of the wave morphology analysis units 712 (FIG. 7). It should also be noted, however, that certain software can also be used to advantageous effect in this context.

Figure 12:
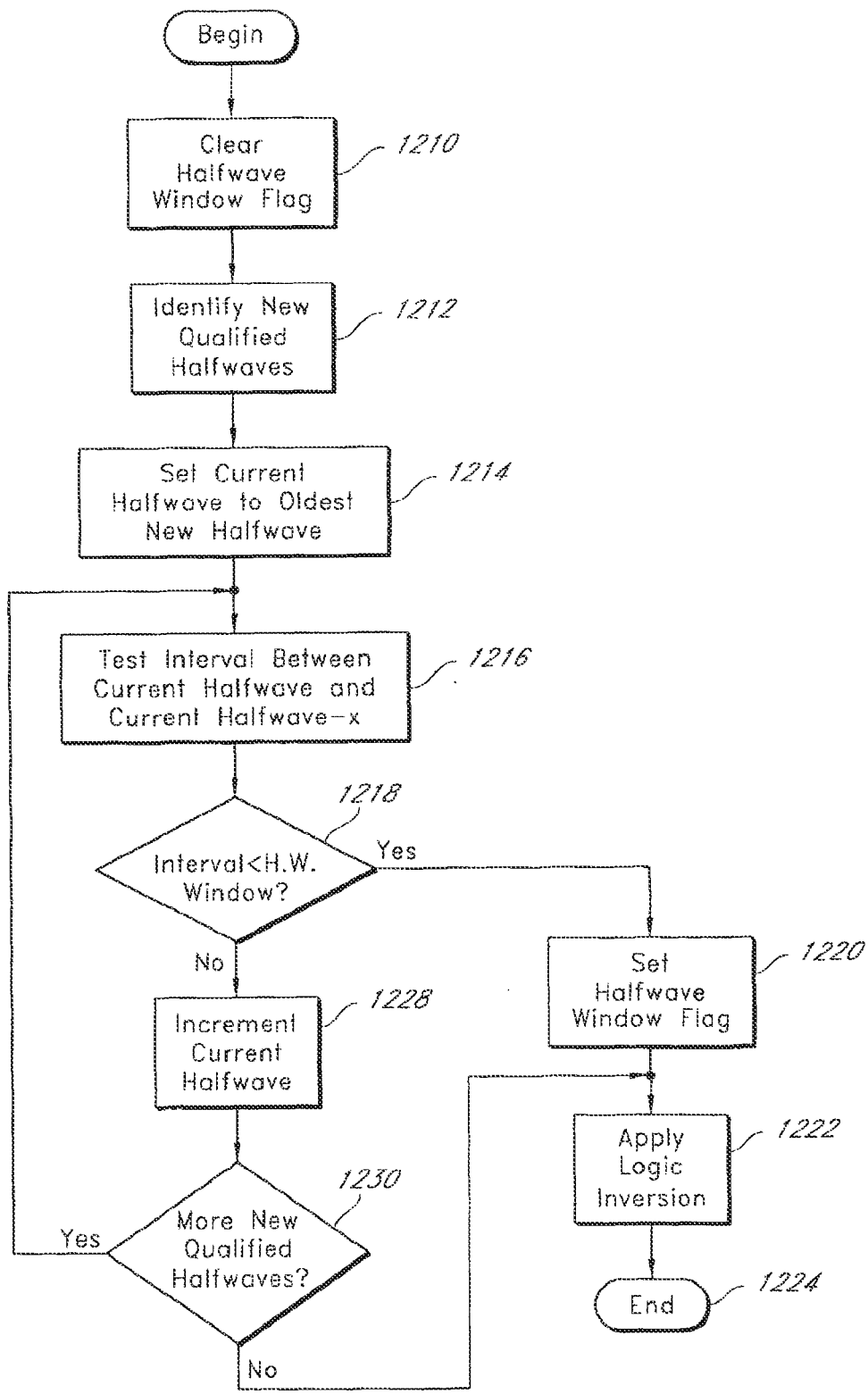
FIG. 12 is a flow chart illustrating the process performed by software in the central processing unit in extracting and analyzing half waves from an EEG signal.

This stored information is used in the software process illustrated in FIG. 12, which is performed on a periodic basis, preferably once every processing window (a recurring time interval that is either fixed or programmable) by a system according to some embodiments. Consistent with the other analysis tools described herein, the duration of an exemplary processing window is in one embodiment, 128 ms, which corresponds to 32 samples at a 250 Hz sampling rate.

Each time the software process of FIG. 12 is invoked, the half wave window flag is first cleared (step 1210). Any qualified half waves identified by the process set forth in FIG. 11 that are newly identified since the last invocation of the procedure (i.e., all qualified half waves that ended within the preceding processing window) are identified (step 1212). A "current half wave" pointer is set to point to the oldest qualified half wave identified in the most recent processing window (step 1214). The time interval between the current half wave and the prior x half waves is then measured (step 1216), where x is a specified minimum number of half waves (preferably a programmable value) to be identified within a selected half wave time window (the duration of which is another programmable value) to result in the possible detection of a neurological event. If the time interval is less than the duration of the half wave time window (step 1218), then the half wave window flag is set (step 1220), logic inversion is selectively applied (step 1222), and the procedure ends (step 1224). Logic inversion, a mechanism for determining whether an analysis unit is triggered by the presence or absence of a condition, is explained in greater detail below. Otherwise, the current half wave pointer is incremented to point to the next new half wave (step 1228), and if there are no more new half waves (step 1230), logic inversion is applied if desired (step 1222), and the procedure ends (step 1224). Otherwise, the next time interval is tested (step 1216) and the process continues from there.

Logic inversion allows the output flag for the wave morphology analysis unit (or any other analyzer) to be selectively inverted. If logic inversion is configured to be applied to an output of a particular analysis unit, then the corresponding flag will be clear when the detection criterion (e.g., number of qualified half waves) is met, and set when the detection criterion is not met. This capability provides some additional flexibility in configuration, facilitating detection of the absence of certain signal characteristics when, for example, the presence of those characteristics is the norm.

Figure 13:
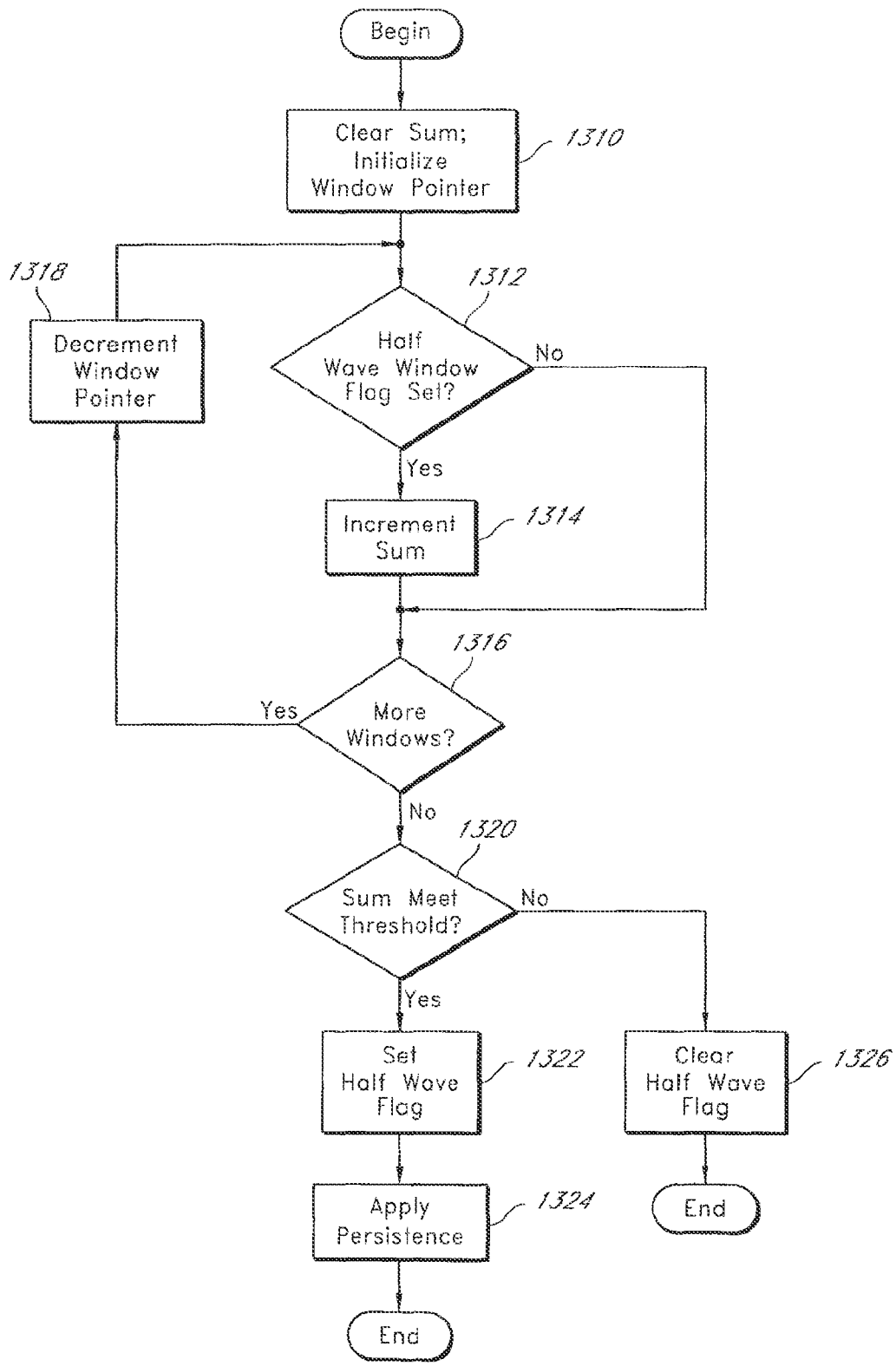
FIG. 13 is a flow chart illustrating the process performed by software in the central processing unit in the application of an X of Y criterion to half wave windows.

In some embodiments, the half wave window flag (set in step 1220) indicates whether a sufficient number of qualified half waves occur over an interval ending in the most recent processing window. To reduce the occurrence of spurious detections, an X of Y criterion is applied, causing the wave morphology analysis unit to trigger only if a sufficient number of qualified half waves occur in X of the Y most recent processing windows, where X and Y are parameters individually adjustable for each analysis tool. This process is illustrated in FIG. 13.

Initially, a sum (representing recent processing windows having the half wave window flag set) is cleared to zero and a current window pointer is initialized to point to the most recent processing window (step 1310). If the half wave window flag corresponding to the current window pointer is set (step 1312), then the sum is incremented (step 1314). If there are more processing windows to examine (for an X of Y criterion, a total of Y processing windows, including the most recent, should be considered) (step 1316), then the window pointer is decremented (step 1318) and the flag testing and sum incrementing steps (steps 1312-1314) are repeated.

After Y windows have been considered, if the sum of windows having set half wave window flags meets the threshold X (step 1320), then the half wave analysis flag is set (step 1322), persistence (described below) is applied (step 1324), and the procedure is complete. Otherwise, the half wave analysis flag is cleared (step 1326).

Persistence, another per-analysis-tool setting, allows the effect of an event detection (a flag set) to persist beyond the end of the detection window in which the event occurs. In some embodiments, persistence can be set anywhere from one second to fifteen seconds (though other settings are possible), so if detections with multiple analysis tools do not all occur simultaneously (though they should still occur within a fairly short time period), a Boolean combination of flags will still yield positive results. Persistence can also be used with a single analysis tool to smooth the results.

When the process of FIG. 13 is completed, the half wave analysis flag (set or cleared in steps 1322 and 1326, respectively) indicates whether an event has been detected in the corresponding channel of the wave morphology analysis units 712, or stated another way, whether a sufficient number of qualified half waves have appeared in X of the Y most recent processing windows. Although in the disclosed embodiment, the steps of FIGS. 12 and 13 are performed in software, it should be recognized that some or all of those steps can be performed using custom electronics, if it proves advantageous in the desired application to use such a configuration.

Figure 14:
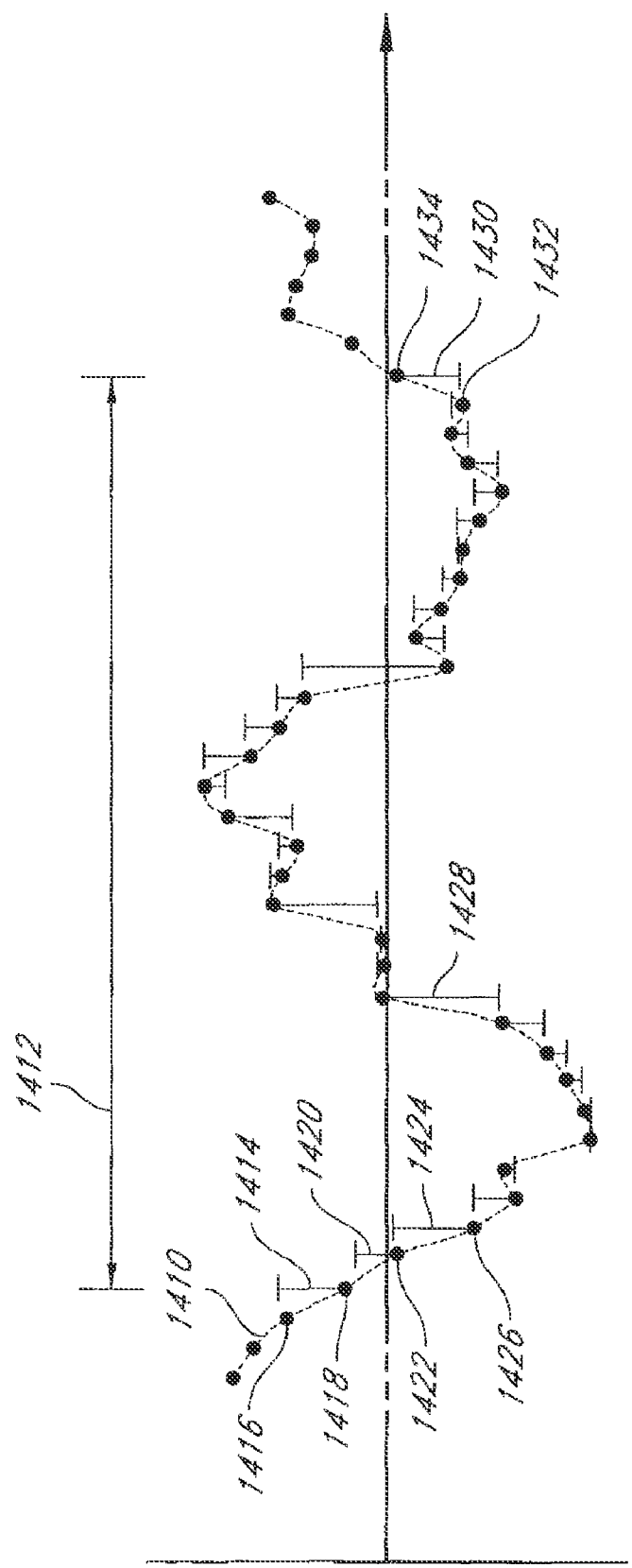
FIG. 14 is a graph of the exemplary EEG signal of FIG. 9, illustrating the calculation of a line length function.

FIG. 14 illustrates the waveform of FIG. 9, further depicting line lengths identified within a time window. The time window used with respect to FIGS. 14-16 may be different from the half wave processing window described above in connection with FIGS. 12-13, but in some embodiments, refers to the same time intervals. From an implementation standpoint, a single device interrupt upon the conclusion of each processing window allows all of the analysis tools to perform the necessary corresponding software processes; the line length analysis process of FIG. 16 (described below) is one such example. A waveform 1410 is a filtered and otherwise pre-processed EEG signal as received in one of the window analysis units 714 from the sensing front end 512. As discussed above, line lengths are considered within time windows. As illustrated in FIG. 14, the duration of an exemplary window 1412 is 32 samples, which is equivalent to 128 ms at a 250 Hz sampling rate.

The total line length for the window 1412 is the sum of the sample-to-sample amplitude differences within that window 1412. For example, the first contribution to the line length within the window 1412 is a first amplitude difference 1414 between a previous sample 1416 occurring immediately before the window 1412 and a first sample 1418 occurring within the window 1412. The next contribution comes from a second amplitude difference 1420 between the first sample 1418 and a second sample 1422; a further contribution 1424 comes from a third amplitude difference between the second sample 1422 and a third sample 1426; and so on. At the end of the window 1412, the final contribution to the line length comes from a last amplitude difference 1430 between a second-last sample 1432 in the window 1412 and a last sample 1434 in the window 1412. Note that all line lengths, whether increasing or decreasing in direction, are accumulated as positive values; accordingly, a decreasing amplitude difference 1414 and an increasing amplitude difference 1428 both contribute to a greater line length.

As illustrated herein, and as discussed in detail above, there are thirty-two samples within the window 1412. The illustrated window 1412 has a duration of 128 ms, and accordingly, the illustrated sample rate is 250 Hz. It should be noted, however, that alternate window durations and sample rates are possible and considered to be appropriate for some embodiments.

Figure 15:
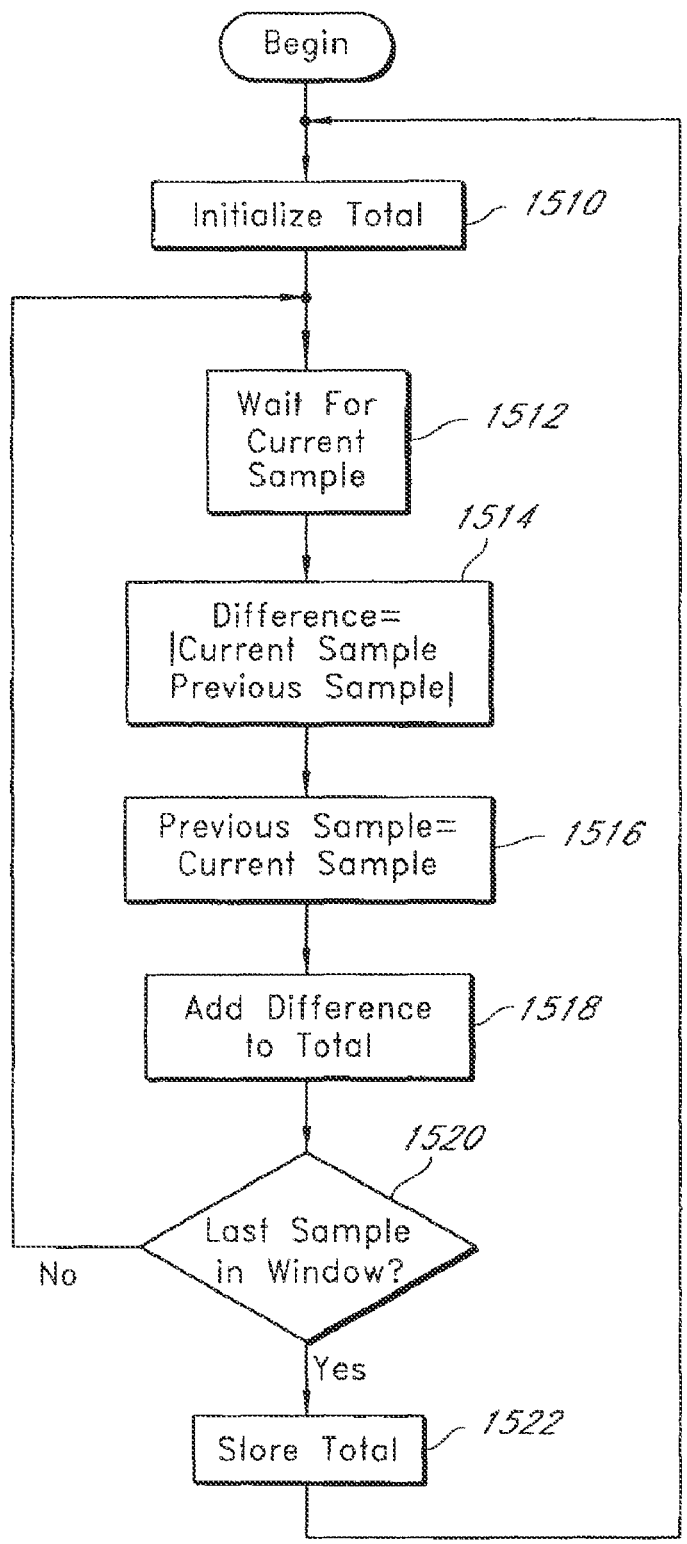
FIG. 15 is a flow chart illustrating the process performed by hardware functional components of the waveform analyzer of FIG. 7 in calculating the line length function as illustrated in FIG. 14.

The line lengths illustrated in FIG. 14 can be calculated as shown by the flow chart of FIG. 15, which is invoked at the beginning of a time window. Initially, a line length total variable is initialized to zero (step 1510). The current sample is awaited (step 1512), and the absolute value of the amplitude difference between the current sample and the previous sample (which, when considering the first sample in a window, may come from the last sample in a previous window) is measured (step 1514).

In various alternative embodiments, either the measured difference (as calculated in step 1514, described above), or the sample values used to calculate the difference can be mathematically transformed in useful nonlinear ways. For example, it may be advantageous in certain circumstances to calculate the difference between adjacent samples using the squares of the sample values, or to calculate the square of the difference between sample values, or both. It is contemplated that other transformations (such as square root, exponentiation, logarithm, and other nonlinear functions) might also be advantageous in certain circumstances. Whether or not to perform such a transformation and the nature of any transformation to be performed are preferably programmable parameters of the device 110.

For use in the next iteration, the previous sample is replaced with the value of the current sample (step 1516), and the calculated absolute value is added to the total (step 1518). If there are more samples remaining in the window 1412 (step 1520), another current sample is awaited (step 1512) and the process continues. Otherwise, the line length calculation for the window 1412 is complete, and the total is stored (step 1522), the total is re-initialized to zero (step 1510), and the process continues.

As with the half wave analysis method set forth above, the line length calculation does not need to terminate; it can be free-running yet interruptible. If the line length calculation is restarted after having been suspended, it should be re-initialized and restarted at the beginning of a window. This synchronization can be accomplished through hardware interrupts.

Figure 16:
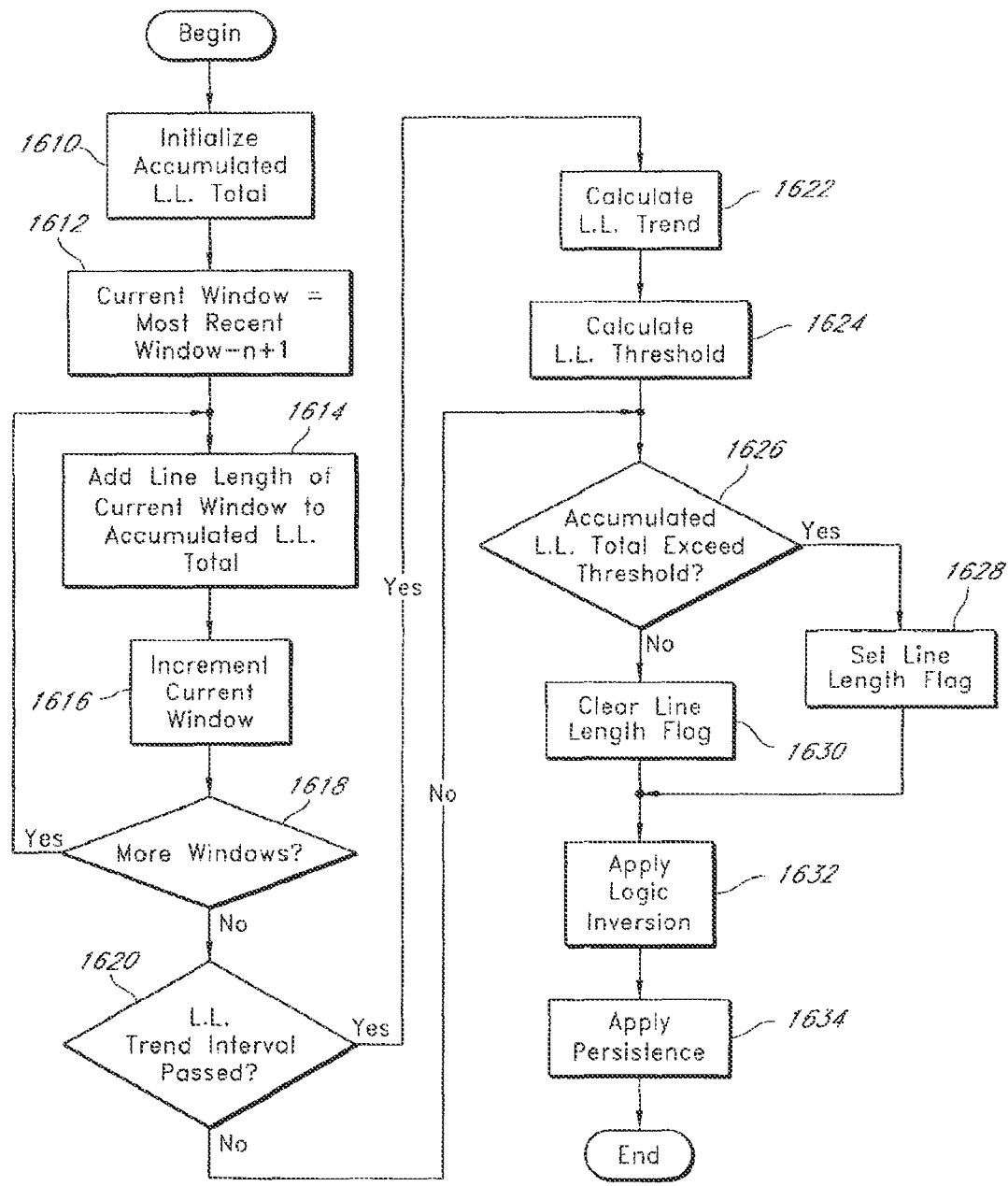
FIG. 16 is a flow chart illustrating the process performed by software in the central processing unit in calculating and analyzing the line length function of an EEG signal.

The line lengths calculated as shown in FIG. 15 are then processed as indicated in the flow chart of FIG. 16, which is performed after each window 1412 is calculated and stored (step 1522).

The process begins by calculating a running accumulated line length total over a period of n time windows. Where n>1, the effect is that of a sliding window; in an alternative embodiment an actual sliding window processing methodology may be used. First, the accumulated total is initialized to zero (step 1610). A current window pointer is set to indicate the $n^{th}$-last window, i.e., the window (n-1) windows before the most recent window (step 1612). The line length of the current window is added to the total (step 1614), the current window pointer is incremented (step 1616), and if there are more windows between the current window pointer and the most recent (last) window (step 1618), the adding and incrementing steps (1614-1616) are repeated. Accordingly, by this process, the resulting total includes the line lengths for each of the n most recent windows.

In some embodiments, the accumulated total line length is compared to a dynamic threshold, which is based on a trend of recently observed line lengths. The trend is recalculated regularly and periodically, after each recurring line length trend interval (which is preferably a fixed or programmed time interval). Each time the line length trend interval passes (step 1620), the line length trend is calculated or updated (step 1622). In some embodiments, this is accomplished by calculating a normalized moving average of several trend samples, each of which represents several consecutive windows of line lengths. A new trend sample is taken and the moving average is recalculated upon every line length trend interval. The number of trend samples used in the normalized moving average and the number of consecutive windows of line length measurements per trend sample are preferably both fixed or programmable values.

After the line length trend has been calculated, the line length threshold is calculated (step 1624) based on the new line length trend. In some embodiments, the threshold can be set as either a percentage of the line length trend (either below 100% for a threshold that is lower than the trend, or above 100% for a threshold that is higher than the trend) or alternatively a fixed numeric offset from the line length trend (either negative for a threshold that is lower than the trend, or positive for a threshold that is higher than the trend). Other methods for deriving a numeric threshold from a numeric trend can also be used in accordance with some embodiments.

The first time the process of FIG. 16 is performed, there is generally no line length trend against which to set a threshold. Accordingly, for the first several passes through the process (until a sufficient amount of EEG data has been processed to establish a trend), the threshold is essentially undefined and the line length detector should not return a positive detection. Some "settling time" thus can be used to establish trends and thresholds before detections are made.

If the accumulated line length total exceeds the calculated threshold (step 1626), then a flag is set (step 1628) indicating a line-length-based event detection on the current window analysis unit channel 714. As described above, in some embodiments, the threshold is dynamically calculated from a line length trend, but alternatively, the threshold may be static, either fixed or programmed into the device 110. If the accumulated line length total does not exceed the threshold, the flag is cleared (step 1630). Once the line length flag has been either set or cleared, logic inversion is applied (step 1632), persistence is applied (step 1634), and the procedure terminates.

The resulting persistent line length flag indicates whether the threshold has been exceeded within one or more windows over a time period corresponding to the line length flag persistence. As discussed in further detail below, line length event detections can be combined with the half wave event detections, as well as any other applicable detection criteria according to some embodiments.

Figure 17:
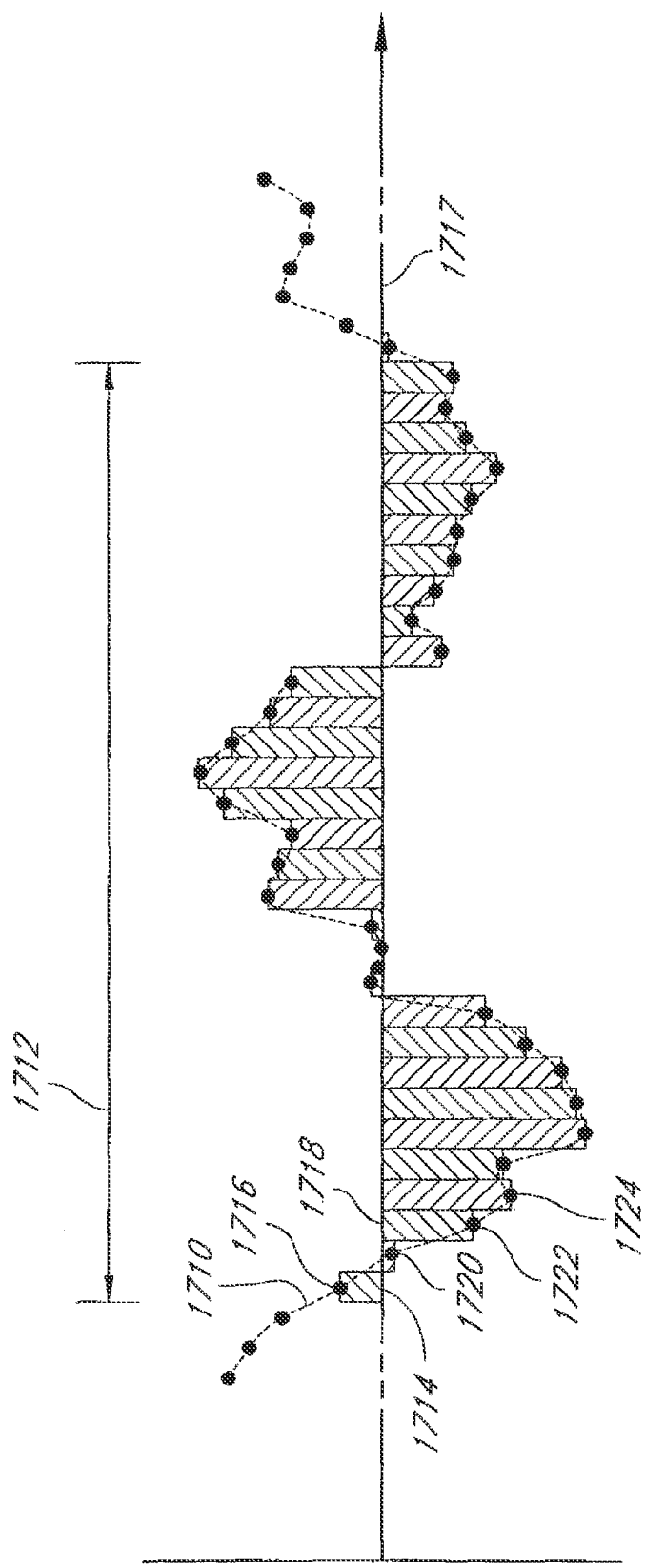
FIG. 17 is a graph of the exemplary EEG signal of FIG. 9, illustrating the calculation of an area function.

FIG. 17 illustrates the waveform of FIG. 9 with area under the curve identified within a window. Area under the curve, which in some circumstances is somewhat representative of a signal's energy (though energy of a waveform is more accurately represented by the area under the square of a waveform), is another detection criterion that can be used in accordance with some embodiments.

The total area under the curve represented by a waveform 1710 within the window 1712 is equal to the sum of the absolute values of the areas of each rectangular region of unit width vertically bounded by the horizontal axis and the sample. For example, the first contribution to the area under the curve within the window 1712 comes from a first region 1714 between a first sample 1716 and a baseline 1717. A second contribution to the area under the curve within the window 1712 comes from a second region 1718, including areas between a second sample 1720 and the baseline 1717. There are similar regions and contributions for a third sample 1722 and the baseline 1717, a fourth sample 1724 and the baseline 1717, and so on. It should be observed that the region widths are not important—the area under each sample can be considered the product of the sample's amplitude and a unit width, which can be disregarded. In a similar manner, each region is accumulated and added to the total area under the curve within the window 1712. Although the concept of separate rectangular regions is a useful construct for visualizing the idea of area under a curve, it should be noted that a process for calculating area need not partition areas into regions as shown in FIG. 17—it is only necessary to accumulate the absolute value of the waveform's amplitude at each sample, as the unit width of each region can be disregarded. The process for doing this will be set forth in detail below in connection with FIG. 18.

Figure 18:
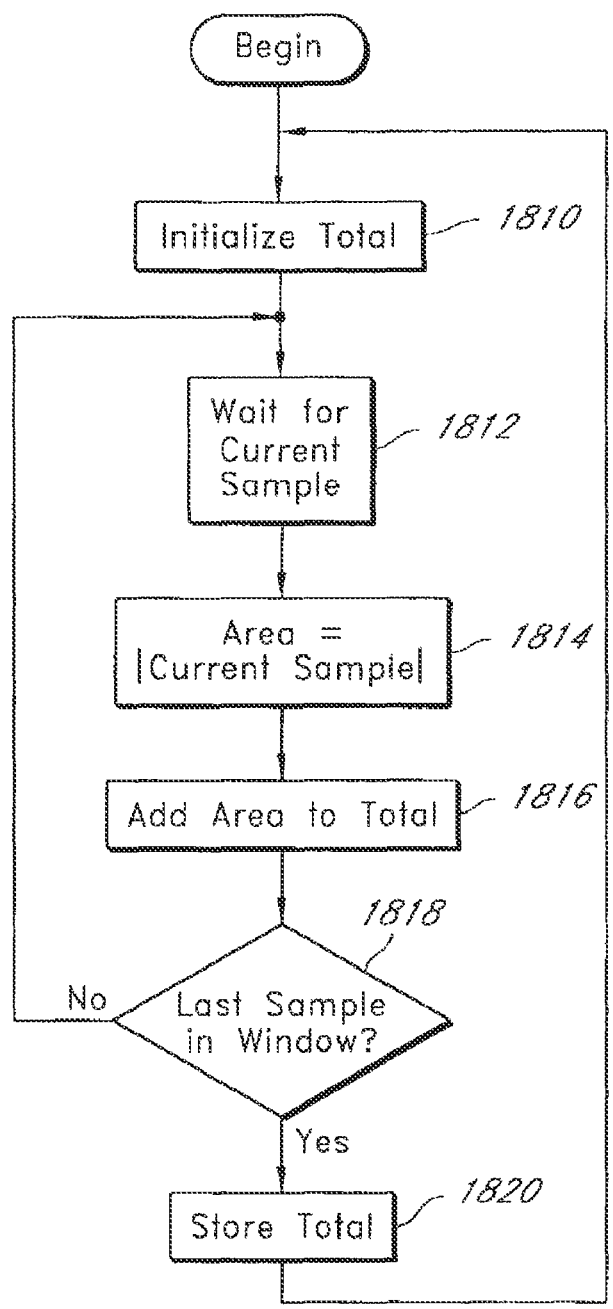
FIG. 18 is a flow chart illustrating the process performed by hardware functional components of the waveform analyzer of FIG. 7 in calculating the area function as illustrated in FIG. 17.

The areas under the curve illustrated in FIG. 17 are calculated as shown by the flow chart of FIG. 18, which is invoked at the beginning of a time window. Initially, an area total variable is initialized to zero (step 1810). The current sample is awaited (step 1812), and the absolute value of the current sample is measured (step 1814).

As with the line length calculation method described above (with reference to FIG. 15), in various alternative embodiments, the current sample (as measured in step 1814, described above) may be mathematically transformed in useful nonlinear ways. For example, it may be advantageous in certain circumstances to calculate the square of the current sample rather than its absolute value. The result of such a transformation by squaring each sample will generally be more representative of signal energy, though it is contemplated that other transformations (such as square root, exponentiation, logarithm, and other nonlinear functions) might also be advantageous in certain circumstances. Whether or not to perform such a transformation and the nature of any transformation to be performed are preferably programmable parameters of the device 110.

The calculated absolute value is added to the total (step 1816). If there are more samples remaining in the window 1712 (step 1818), another current sample is awaited (step 1812) and the process continues. Otherwise, the area calculation for the window 1712 is complete, and the total is stored (step 1820), the total is reinitialized to zero (step 1810), and the process continues.

As with the half wave and line length analysis methods set forth above, the area calculation does not need to terminate; it can be free-running yet interruptible. If the area calculation is restarted after having been suspended, it should be re-initialized and restarted at the beginning of a window. This synchronization can be accomplished through hardware interrupts.

Figure 19:
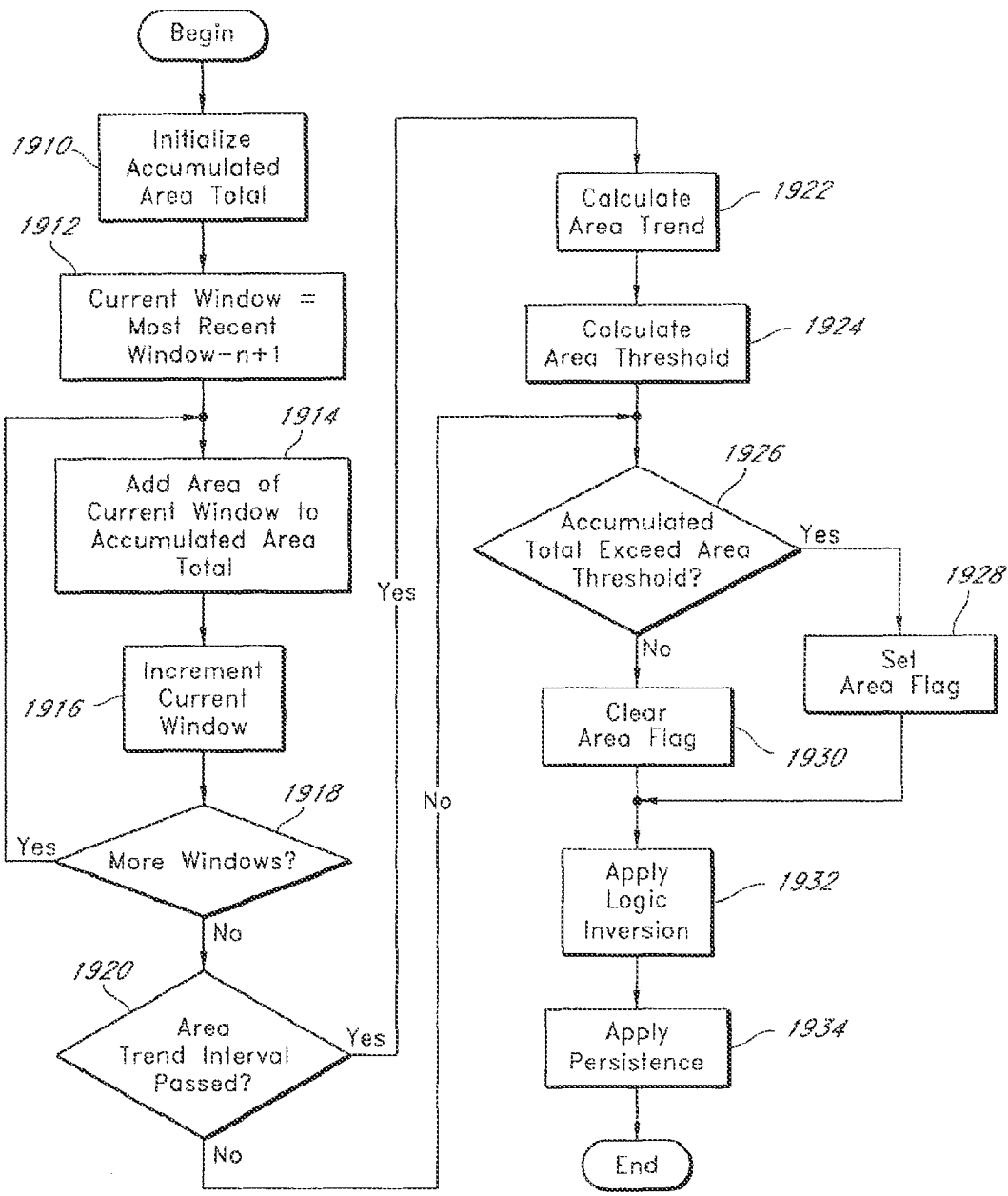
FIG. 19 is a flow chart illustrating the process performed by software in the central processing unit in calculating and analyzing the area function of an EEG signal.

The line lengths calculated as shown in FIG. 18 are then processed as indicated in the flow chart of FIG. 19, which is performed after each window 1712 is calculated and stored (step 1820).

The process begins by calculating a running accumulated area total over a period of n time windows. Where n>1, the effect is that of a sliding window; in an alternative embodiment an actual sliding window processing methodology may be used. First, the accumulated total is initialized to zero (step 1910). A current window pointer is set to indicate the $n^{th}$-last window, i.e., the window (n−1) windows before the most recent window (step 1912). The area for the current window is added to the total (step 1914), the current window pointer is incremented (step 1916), and if there are more windows between the current window and the most recent (last) window (step 1918), the adding and incrementing steps (1914-1916) are repeated. Accordingly, by this process, the resulting total includes the areas under the curve for each of the n most recent windows.

In some embodiments, the accumulated total area can be compared to a dynamic threshold, which can be based on a trend of recently observed areas. The trend can be recalculated regularly and periodically, after each recurring area trend interval (which is preferably a fixed or programmed time interval). Each time the area trend interval passes (step 1920), the area trend can be calculated or updated (step 1922). In some embodiments, this can be accomplished by calculating a normalized moving average of several trend samples, each of which represents several consecutive windows of areas. A new trend sample can be taken and the moving average is recalculated upon every area trend interval. The number of trend samples used in the normalized moving average and the number of consecutive windows of area measurements per trend sample are preferably both fixed or programmable values.

After the area trend has been calculated, the area threshold can be calculated (step 1924) based on the new area trend. As with line length, discussed above, the threshold can be set as either a percentage of the area trend (either below 100% for a threshold that is lower than the trend, or above 100% for a threshold that is higher than the trend) or alternatively a fixed numeric offset from the area trend (either negative for a threshold that is lower than the trend, or positive for a threshold that is higher than the trend).

The first time the process of FIG. 19 is performed, there is generally no area trend against which to set a threshold. Accordingly, for the first several passes through the process (until a sufficient amount of EEG data has been processed to establish a trend), the threshold is essentially undefined and the area detector should not return a positive detection. Some "settling time" thus can be used to establish trends and thresholds before a detection can be made.

If the accumulated total exceeds the calculated threshold (step 1926), then a flag is set (step 1928) indicating an area-based event detection on the current window analysis unit channel 714. Otherwise, the flag is cleared (step 1930). Once the area flag has been either set or cleared, logic inversion is applied (step 1932), persistence is applied (step 1934), and the procedure terminates.

The resulting persistent area flag indicates whether the threshold has been exceeded within one or more windows over a time period corresponding to the area flag persistence. As discussed in further detail below, area event detections can be combined with the half wave event detections, line length event detections, as well as any other applicable detection criteria according to some embodiments.

In some embodiments, each threshold for each channel and each analysis tool can be programmed separately; accordingly, a large number of individual thresholds can be used. It should be noted thresholds can vary widely; they can be updated by a physician via the external programmer 312 (FIG. 3), and some analysis tool thresholds (e.g., line length and area) can also be automatically varied depending on observed trends in the data. This is preferably accomplished based on a moving average of a specified number of window observations of line length or area, adjusted as desired via a fixed offset or percentage offset, and may compensate to some extent for diurnal and other normal variations in brain electrophysiological parameters.

With regard to the flow charts of FIGS. 11-13, 15-16, and 18-19, it should be noted that there can be a variety of ways these processes are implemented. For example, state machines, software, hardware (including ASICs, FPGAs, and other custom electronics), and various combinations of software and hardware, are all solutions that would be possible to practitioners of ordinary skill in the art of electronics and systems design. It should further be noted that the steps performed in software need not be, as some of them can be implemented in hardware, if desired, to further reduce computational load on the processor. In the context of the present embodiments, it is not believed to be advantageous to have the software perform additional steps, as that would likely increase power consumption.

In some embodiments, one of the detection schemes set forth above (e.g., half wave detection) can be adapted to use an X of Y criterion to weed out spurious detections. This can be implemented via a shift register, as usual, or by more efficient computational methods. As described above, half waves are analyzed on a window-by-window basis, and as described above (in connection with FIG. 13), the window results are updated on a separate analysis window interval. If the detection criterion (i.e., a certain number of half waves in less than a specified time period) is met for any of the half waves occurring in the most recent window, then detection is satisfied within that window. If that occurs for at least X of the Y most recent windows, then the half wave analysis tool triggers a detection. If desired, other detection algorithms (such as line length and area) may operate in much the same way: if thresholds are exceeded in at least X of the Y most recent windows, then the corresponding analysis tool triggers a detection.

Also, in the disclosed embodiment, each detection flag, after being set, remains set for a selected amount of time, allowing them to be combined by Boolean logic (as described below) without necessarily being simultaneous.

As indicated above, each of the software processes set forth above (FIGS. 12-13, 16, and 19) correspond to functions performed by the wave morphology analysis units 712 and window analysis units 714. Each one is initiated periodically, typically once per detection window (1212, 1512). The outputs from the half wave and window analysis units 712 and 714, namely the flags generated in response to counted qualified half waves, accumulated line lengths, and accumulated areas are combined to identify event detections as functionally illustrated in FIG. 8 and as described via flow chart in FIG. 20.

The process begins with the receipt of a timer interrupt (step 2010), which is typically generated on a regular periodic basis to indicate the edges of successive time windows. Accordingly, in a system or method in some embodiments, such a timer interrupt is received every 128 ms, or as otherwise programmed or designed. Then the half wave (step 2012, FIGS. 12-13), line length (step 2014, FIG. 16), and area (step 2016, FIG. 19) analysis tools are evaluated with respect to the latest data generated thereby, via the half wave analysis flag, the line length flag, and the area flag for each active channel. The steps of checking the analysis tools (steps 2012, 2014, and 2016) can be performed in any desired order or in parallel, as they are generally not interdependent. It should be noted that the foregoing analysis tools should be checked for every active channel, and may be skipped for inactive detection channels.

Flags, indicating whether particular signal characteristics have been identified in each active channel, for each active analysis tools, can then be combined into detection channels (step 2018) as illustrated in FIG. 8. In some embodiments, this operation is performed as described in detail below with reference to FIG. 21. Each detection channel is a Boolean AND combination of analysis tool flags for a single channel, and as disclosed above, there can be one or more channels in a system according to some embodiments.

The flags for multiple detection channels are then combined into event detector flags (step 2020), which are indicative of identified neurological events calling for action by the device. This process is described below, see FIG. 20, and is in general a Boolean combination of detection channels, if there is more than one channel per event detector.

If an event detector flag is set (step 2022), then a corresponding action is initiated (step 2024) by the device. Actions according to some embodiments can include the presentation of a warning to the patient, an initiation of a device mode change, or a recording of certain EEG signals or other data; it will be appreciated that there are numerous other possibilities. It is preferred, but not necessary, for actions initiated by a device according to some embodiments to be performed in parallel with the sensing and detection operations described in detail herein.

Multiple event detector flags are possible, each one representing a different combination of detection channel flags. If there are further event detector flags to consider (step 2026), those event detector flags can also be evaluated (step 2022) and may cause further actions by the device (step 2024). It should be noted that, in general, actions performed by the device (as in step 2024) may be in part dependent on a device state—even if certain combinations of events do occur, no action may be taken if the device is in an inactive state, for example.

Figure 20:
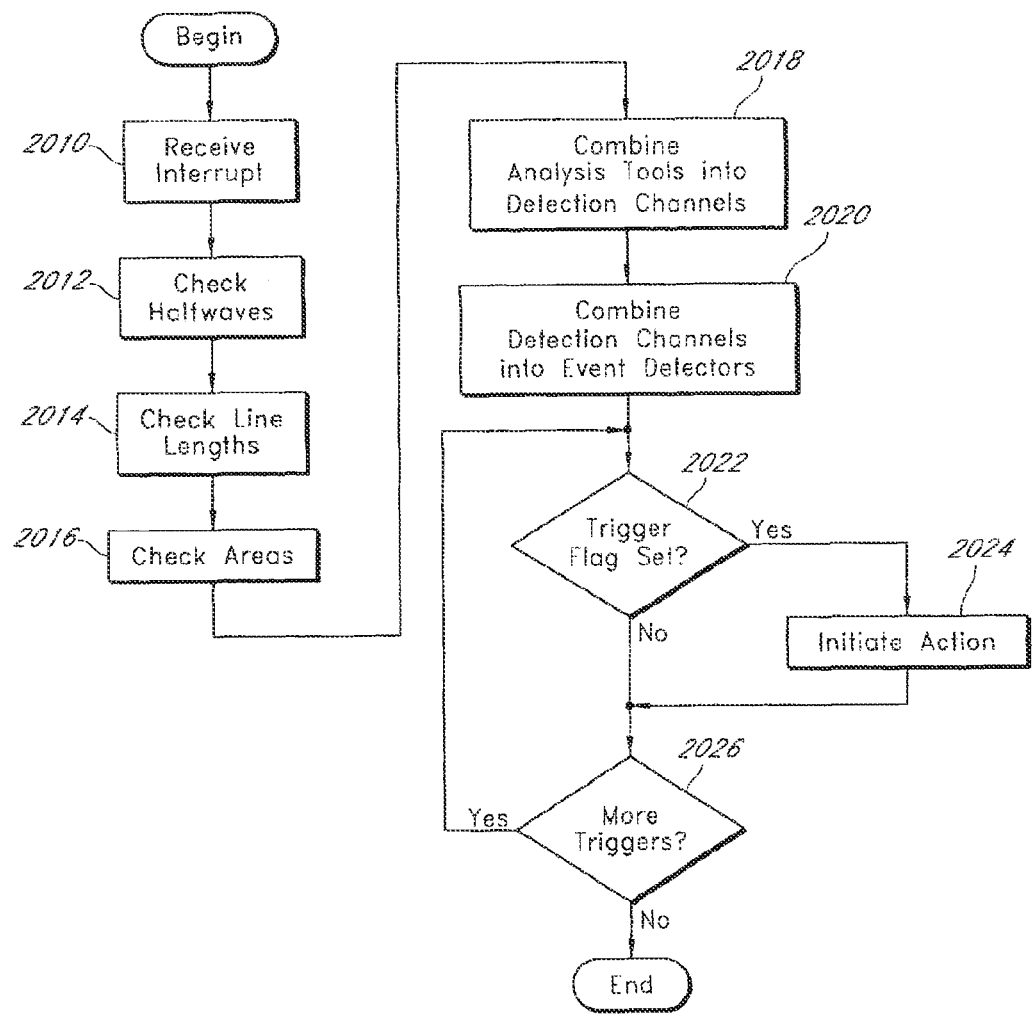
FIG. 20 is a flow chart illustrating the process performed by event-driven software in the central processing unit to analyze half wave, line length, and area information for detection according to an embodiment.
Figure 21:
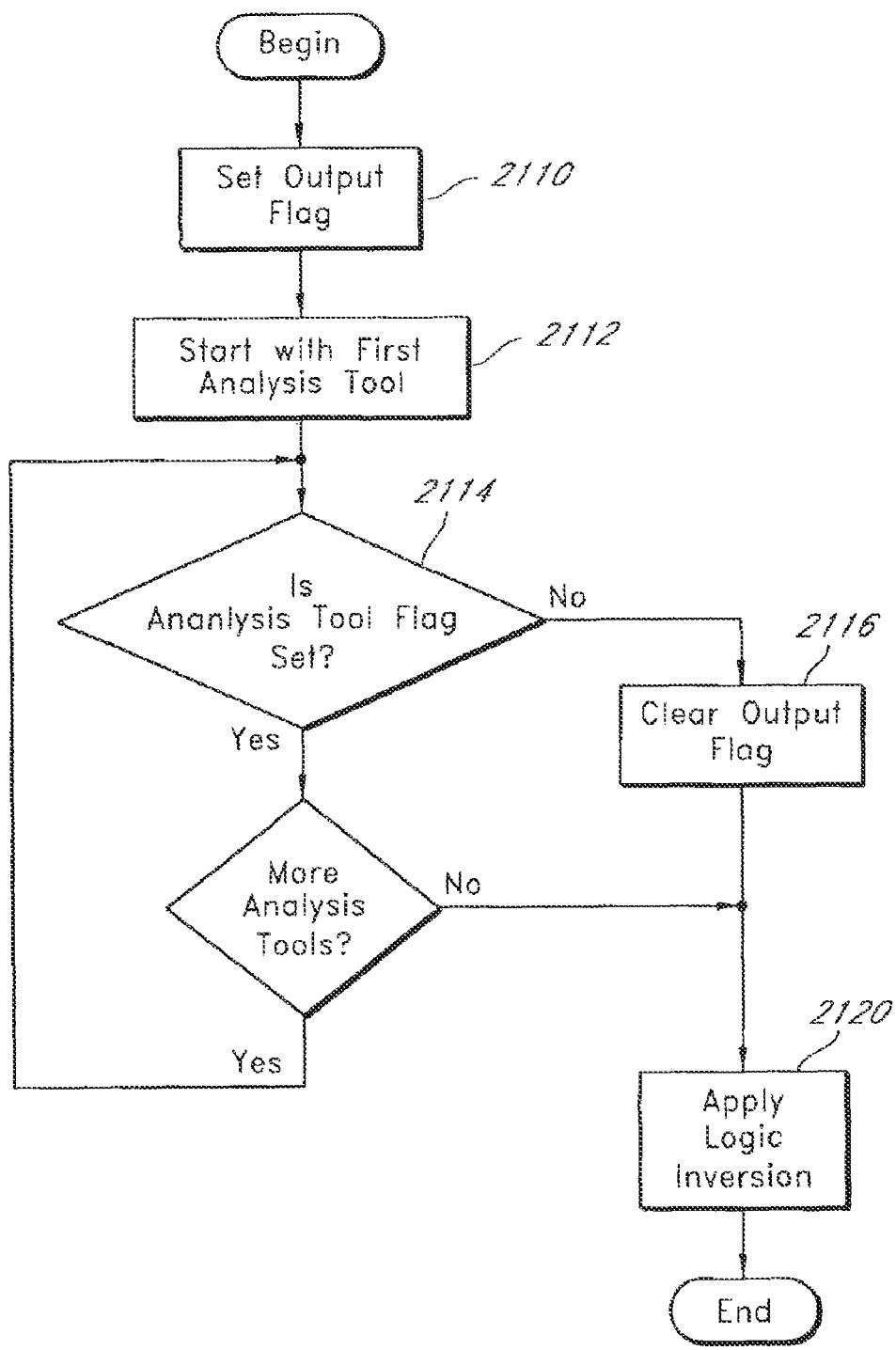
FIG. 21 is a flow chart illustrating the combination of analysis tools into detection channels in an embodiment.

As described above, and as illustrated in FIG. 20 as step 2018, a corresponding set of analysis tool flags is combined into a detection channel flag as shown in FIG. 21 (see also FIG. 8). Initially the output detection channel flag is set (step 2110). Beginning with the first analysis tool for a particular detection channel (step 2112), if the corresponding analysis tool flag is not set (step 2114), then the output detection channel flag is cleared (step 2116).

If the corresponding analysis tool flag is set (step 2114), the output detection channel flag remains set, and further analysis tools for the same channel, if any (step 2118), are evaluated. Accordingly, this combination procedure operates as a Boolean AND operation—if any of the enabled and active analysis tools for a particular detection channel does not have a set output flag, then no detection channel flag is output by the procedure.

A clear analysis tool flag indicates that no detection has been made within the flag persistence period, and for those analysis tools that employ an X of Y criterion, that such criterion has not been met. In certain circumstances, it may be advantageous to also provide detection channel flags with logic inversion. Where a desired criterion (i.e., combination of analysis tools) is not met, the output flag is set (rather than cleared, which is the default action). This can be accomplished by providing selectable Boolean logic inversion (step 2120) corresponding to each event detector.

Figure 22:
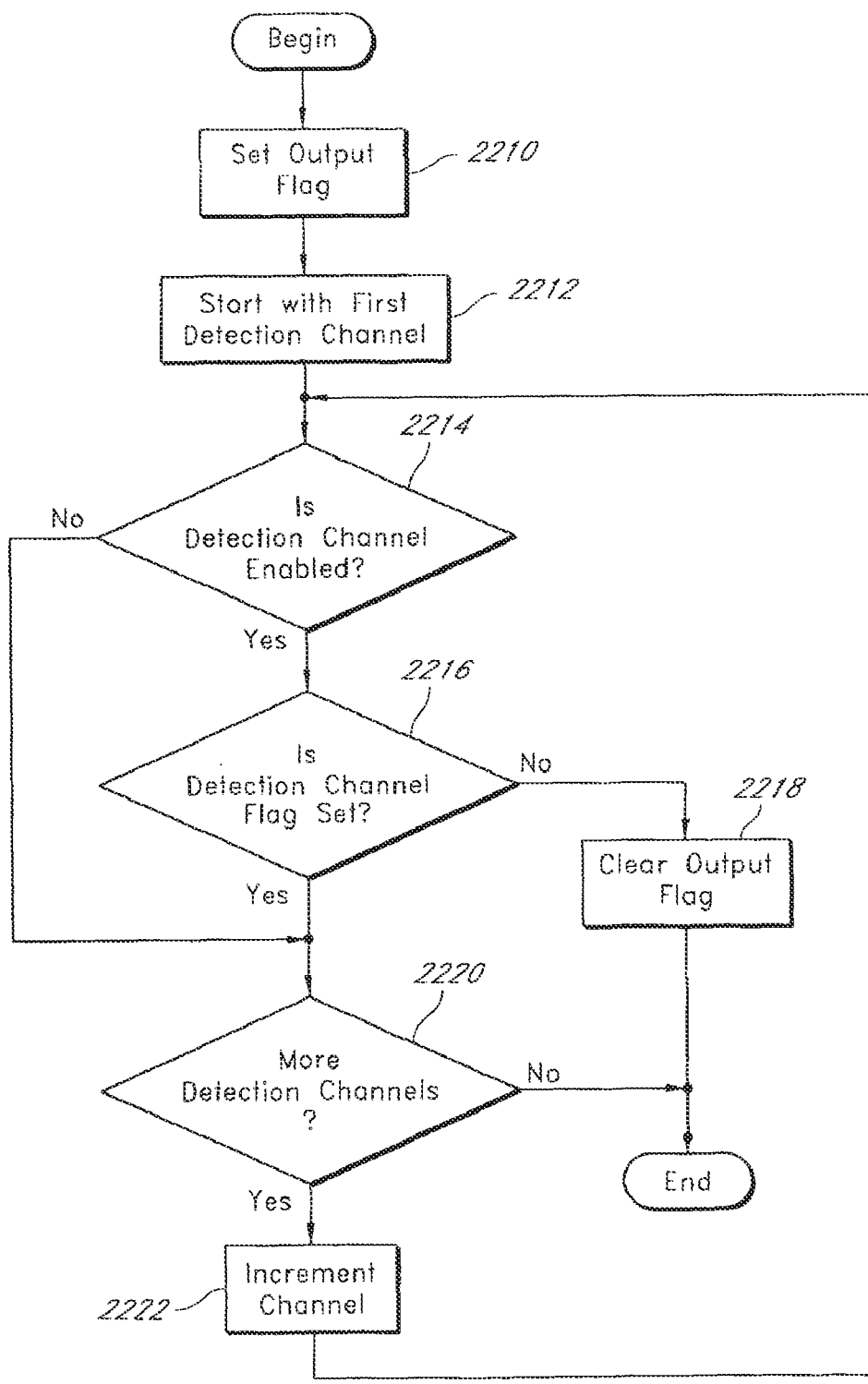
FIG. 22 is a flow chart illustrating the combination of detection channels into event detectors in an embodiment.

Also as described above, and as illustrated in FIG. 20 as step 2020, multiple detection channel flags are combined into a single event detector flag as shown in FIG. 22 (see also FIG. 8). Initially the output event detector flag is set (step 2210). Beginning with the first detection channel for a particular event detector (step 2212), if the channel is not enabled (step 2214), then no check is made. If the channel is enabled and the corresponding detection channel flag is not set (step 2216), then the output event detector flag is cleared (step 2218) and the combination procedure exits. If the corresponding detection channel flag is set (step 2216), the output event detector flag remains set, and further detection channels, if any (step 2220), are evaluated after incrementing the channel being considered (step 2222). Accordingly, this combination procedure also operates as a Boolean AND operation—if any of the enabled and active detection channels does not have a set output flag, then no event detector flag is output by the procedure. It should also be observed that a Boolean OR combination of detection channels may provide useful information in certain circumstances; a software or hardware flow chart accomplishing such a combination is not illustrated, but could easily be created by an individual of ordinary skill in digital electronic design or computer programming.

With reference again to FIG. 20, in some embodiments, the actions taken in the step 2024 can include logging the event flags, logging a summary of the event flags, logging a single event as a result of one or more flags being set, saving the EEG signals detected by the channel, saving portions of EEG signals detected before, during, or after any of the above-noted flags are set, and recording or saving any data generated during the analysis of waveforms noted above, and the like.

Figure 23:
FIG. 23 is an exemplary log of data indicative of the occurrence of neurological events that can be used in conjunction with the recording devices disclosed herein.

In some embodiments, such data can be saved in the memory 516, or any other memory device included in the device 110, in the form of tabulated data, or in any other form. An exemplary data table 2300 is illustrated in FIG. 23. In some embodiments, the tabulated data can include a date stamp indicating the date upon which a neurological event, such as those associated with the above-noted detection flags, is detected. Further, the data can include a time stamp indicating the time at which one of the above-noted flags is set.

Figure 23A:
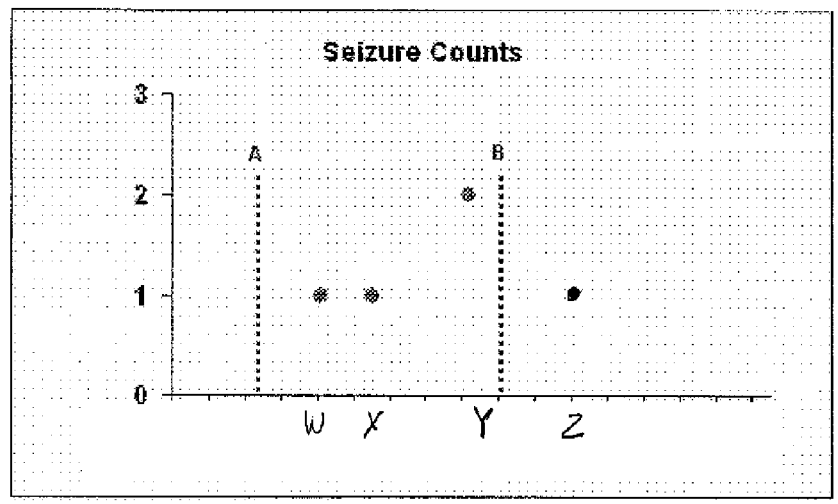
FIG. 23A is an exemplary seizure report that can be generated based on information gathered by any of the implantable recording devices illustrated in these figures.
Figure 23A:
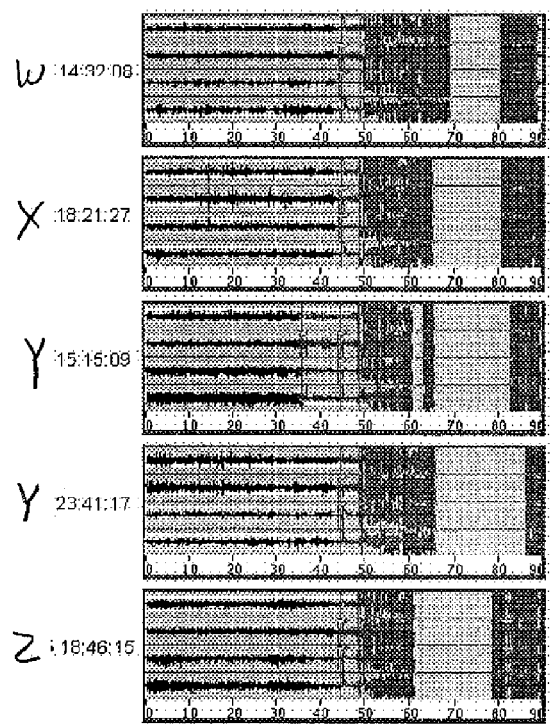

FIG. 23A illustrates an exemplary but nonlimiting example of a report that can be generated with data collected by the implantable seizure monitor 110. At the top of the exemplary report of FIG. 23A are a number of data fields that can include, for example, but without limitation, the patient's name, the date of the report, the name of the physician, the date range during which recordings were taken, and a key identifying when medications have changed or when other clinically significant events occur.

Below these data fields is a chart indicating the number of seizures identified by the implantable recording device 110. This chart is labeled "seizure counts". The vertical axis of this graph indicates the number of seizures counted. The horizontal axis can serve as a timeline. In this case, the days on which seizures were counted are identified as Day W, Day X, Day Y, and Day Z. On the days identified as W, X, and Z, one seizure was counted on each day. On the day labeled Day Y, two seizures were counted.

Below the seizure count chart are samples of brainwave recordings that can be captured by the implantable recording device 110. Each of these recordings are identified corresponding to the day and time at which they were recorded.

As noted above, the seizure report of FIG. 23A is merely an exemplary report that can be generated from the data captured by the implantable recording device 110. Other reports can also be generated. Further, such reports can be organized in different ways and can include other or different information.

Such tabulated data can include an indication of the type of flag that has been set, such as, for example, but without limitation, the area flag of step 1928, the set line length flag of step 1628, and the halfway flag of step 1322, and/or other flags.

As shown in FIG. 23, the tabulated data can optionally include an indication of the severity of the neurological event. For example, the routine illustrated in FIG. 19 can be modified to include an additional operation to save to memory the area trend calculated in step 1922. This saved area calculation can then be stored in the table 2300 if the area flag is set in step 1928. Alternatively, other calculations can also be used to create an indication of the severity of the event causing the area flag to be set in step 1928.

Similarly, the routine of FIG. 16 can be modified to include an additional operation of saving the value of the calculation of the line length trend in step 1622. In such embodiments, this routine can also be modified to save the line length trend value calculated from step 1622 of FIG. 16 to the table 2300 when the line length flag is set in steps 1628. However, other calculations can also be used to create an indication of the severity of the neurological event causing the line length flag to be set in step 1628.

Additionally, the routine of FIG. 13 can be further modified to save the value generated from the sum of step 1314 when the half-wave flag is set in step 1322. Additionally, the routine can be modified to save the value of the sum from step 1314 to the table 2300 so as to provide an indication of the severity of the neurological event causing the half-wave flag to be set in step 1322. However, other calculations can also be made to provide an indication of the severity of the event causing the half-wave flag to be set in step 1322.

In some embodiments, the routine of FIG. 20 can be modified to save data associated with half-wave, line length, or area analyses performed in steps 2012, 2014, 2016, or other analyses. For example, the routine of FIG. 20 can be modified to include an additional operation associated with the operation block 2024 in which an event is logged on the table 2300 when any flags are indicated as being set in any of the operation blocks 2012, 2014, 2016. Such a tabulated dataset can include a date stamp and/or time stamp. Further, such a dataset can also include an indication of the severity of the neurological event triggering any of the flags associated with the operation blocks 2012, 2014, 2016, as illustrated in FIG. 23.

In some embodiments, the routine of FIG. 20 can be configured to log a neurological event only if all of a half-wave flag, a line length flag, and an area flag are set as a result of operation blocks 2012, 2014, 2016. This can provide the benefit of saving memory in the memory device 516 by reducing the number of events that are logged. However, other restrictions can also be used. For example, the routine of FIG. 20 can be modified to log an event only if at least two flags are determined as being set through the operation blocks 2012, 2014, 2016. However, other analyses can also be used to determine when to log a neurological event.

Figure 24:
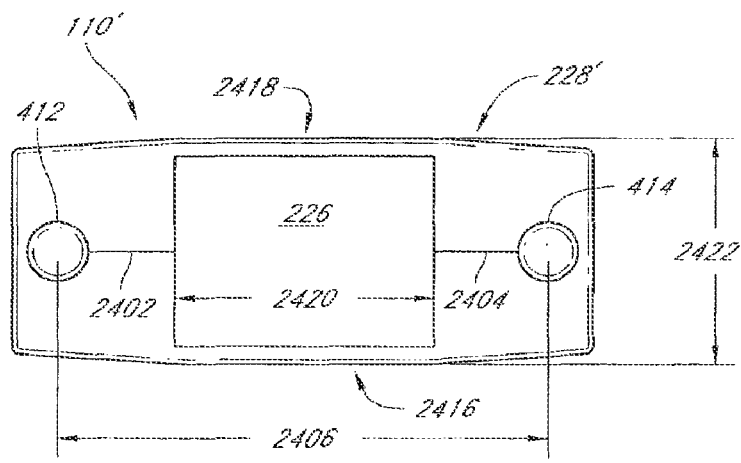
FIG. 24 is a schematic top plan view of an exemplary but nonlimiting embodiment of the implantable recording device having a housing and at least one sensor suspended in a cushioning material.
Figure 25:
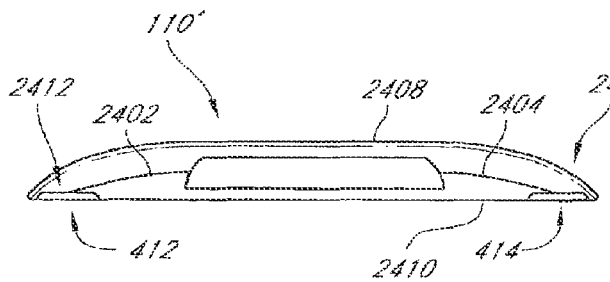
FIG. 25 is a side elevational view of the implantable recording device illustrated in FIG. 23.
Figure 26:
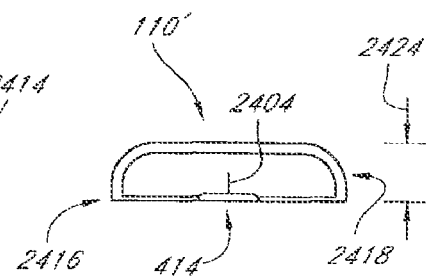
FIG. 26 is a left side elevational view of the implantable recording device of FIG. 23.

FIGS. 24-26 illustrate a modification of the device 110 of FIG. 2 which is identified generally by the reference numeral 110'. The recording device 110' includes some components that can be constructed in accordance with the description noted above with respect to the device 110. Other components of the device 110' also correspond to components of the device 110 but include modifications. As such, those components are identified with the same reference numeral used in FIGS. 2 and 2a except that a "'" has been added.

As shown in FIG. 24, the recording device 110' includes the housing 126 and two sensing electrodes 412, 414 connected to the electronics within the housing through lead wires 2402, 2404. The sensing electrodes 412, 414 are spaced apart by distance identified by the numeral 2406. The distance 2406 can be any amount. However, in an exemplary but nonlimiting embodiment, the distance 2406 can be about 3 centimeters. This spacing provides a balance between signal strength and overall size of the device 110'.

The electrode spacing 2406 should be adequate to sense partial seizures that are only occurring in a limited region of the brain. An example would be a unilateral temporal lobe seizure that does not spread beyond the temporal lobe of onset. Thus, in some embodiments, a spacing 2406 of at least about 3 centimeters as illustrated in FIG. 24 provides a sufficiently strong signal to be analyzed for purposes of detecting desired neurological events. Further, as such, the overall length of the device 110' is not substantially greater than about 3 centimeters. However, as noted above, spacings 2406 of other magnitudes can also be used.

The device 110' also includes a cushion member 228' in which the housing 226 and the sensing electrodes 412, 414, are suspended. In some embodiments, the cushioning member 228' can be a soft silicone rubber material. However, any type of soft biocompatible material can be used as the cushioning member 228'.

As shown in FIGS. 24 and 25, the cushioning member 228' includes an upper outer surface 2408, a lower outer surface 2410, longitudinal end portions 2412, 2414 and front and rear portions 2416, 2418.

Preferably, the housing 226 is suspended within the cushioning member 228' such that no portion of the outer surface of the housing 226 is exposed through the outer surfaces 2408, 2410, 2412, 2414, 2416, 2418 of the cushioning member 228'. This helps provide the patient with enhanced comfort by preventing the hard, and in some embodiments Titanium, outer portions of the housing 226 from contacting the inner layers of the patient's scalp and/or cranium 214 (FIGS. 2 and 2a).

On the other hand, preferably, at least the lower surfaces of the sensing electrodes 412, 414 are exposed through the bottom surface 2410 of the cushioning member 228'. As such, an exposed outer surface of the sensing electrodes 412, 414, can come into direct contact with the inner layers of the patient's scalp, the patient's cranium 214, and/or the patient's dura, which enhances the ability of the sensing electrodes 412, 414 to receive EEG signals.

In the illustrated arrangement of the recording device 110', the sensing electrodes 412, 414 are substantially held in place by the cushioning member 228'. The illustrated configuration of the cushioning member 228' is generally the shape of a pair of wings extending from the housing 226, each of the wings supporting one of the sensing electrodes 412, 414.

Additionally, as shown in FIGS. 24-26, the longitudinal ends 2412, 2414, and the front and rear portions 2416, 2418 of the cushioning member 228' include rounded corners and tapered areas to provide a smooth transition so as to minimize the effect the recording device 110' might have in causing a portion of the patient's scalp protrude.

In an exemplary but nonlimiting embodiment, with the illustrated configuration, the longitudinal length 2420 of the housing 226 can be about 1.5 centimeters. The overall width 2422 of the recording device 110' can be about 1.5 centimeters. Additionally, the sensing electrodes 412, 414, can have a diameter of about 0.4 centimeters. Finally, the overall thickness 2424 (FIG. 26) of the recording device 110' can be about 0.38 centimeters. However, it is to be noted that the above-noted dimensions are merely exemplary, but not limiting, and are intended merely to convey one possible configuration for the recording device 110'. Other configurations, shapes, dimensions, and contours can also be used.

Figure 27:
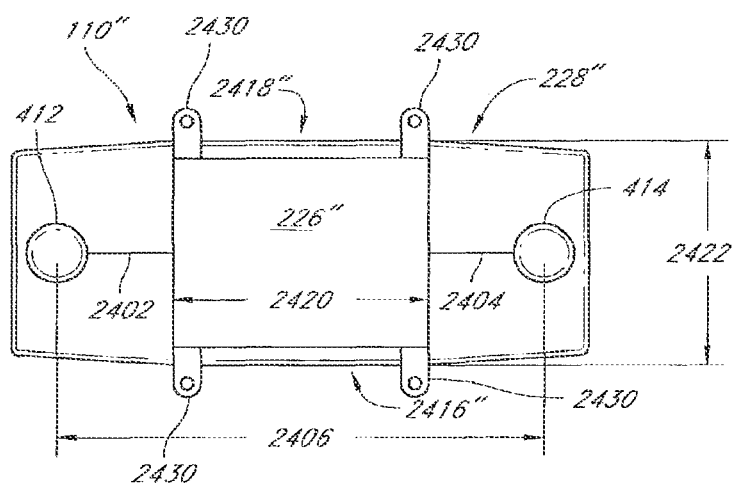
FIG. 27 is a schematic top plan view of a modification of the implantable recording device of FIG. 24.
Figure 28:
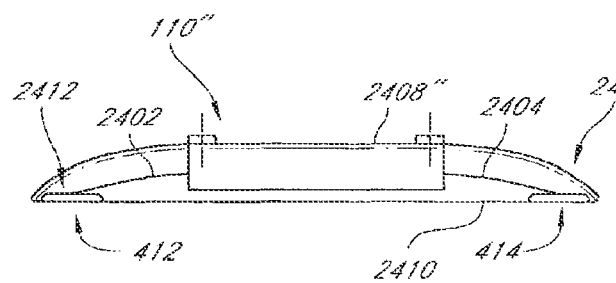
FIG. 28 is a side elevational view of the implantable recording device illustrated in FIG. 27.
Figure 29:
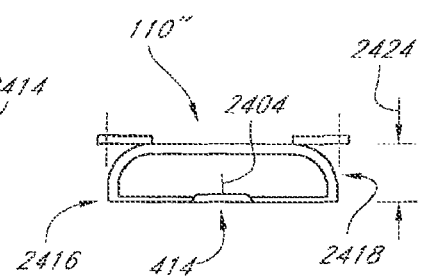
FIG. 29 is a left side elevational view of the implantable recording device of FIG. 27.

FIGS. 27-29 illustrate yet another modification of the implantable seizure recording device 110', which is identified generally by the reference numeral 110". The recording device 110' includes some components that can be constructed in accordance with the description noted above with respect to the devices 110, 110'. Other components of the device 110" also correspond to components of the device 110' but can include modifications. As such, those components are identified with the same reference numerals used in FIG. 2, 2a, or 24-26 except that a "''" has been added thereto.

As shown in FIGS. 27 and 28, the recording device 110" can include at least one mounting tab 2430. In some embodiments, one or more mounting tabs 2430 are mounted at each corner of the housing 226".

The mounting tabs 2430 can have any configuration. In some embodiments, the mounting tabs 2430 project from an upper surface of the housing 226" and include an aperture on a portion of the mounting tabs 2430 that extends outwardly from and outer edge of the housing 226". The mounting tabs 2430 thus can be configured to provide additional anchoring points for securing the recording device 110" to the skull 214 of a patient.

In some embodiments, the mounting tabs 2430 can extend outwardly from the cushioning number 228". In some embodiments, the mounting tabs 2430 can be completely encased in the cushioning member 228". In some embodiments, the top, front, and rear faces of the housing 226 can be left exposed without any of the cushioning member to 228" covering those faces. In such embodiments, it can be more desirable to leave the bottom face of the housing to 226" covered with the cushioning member 228". However, this is optional.

Figure 30:
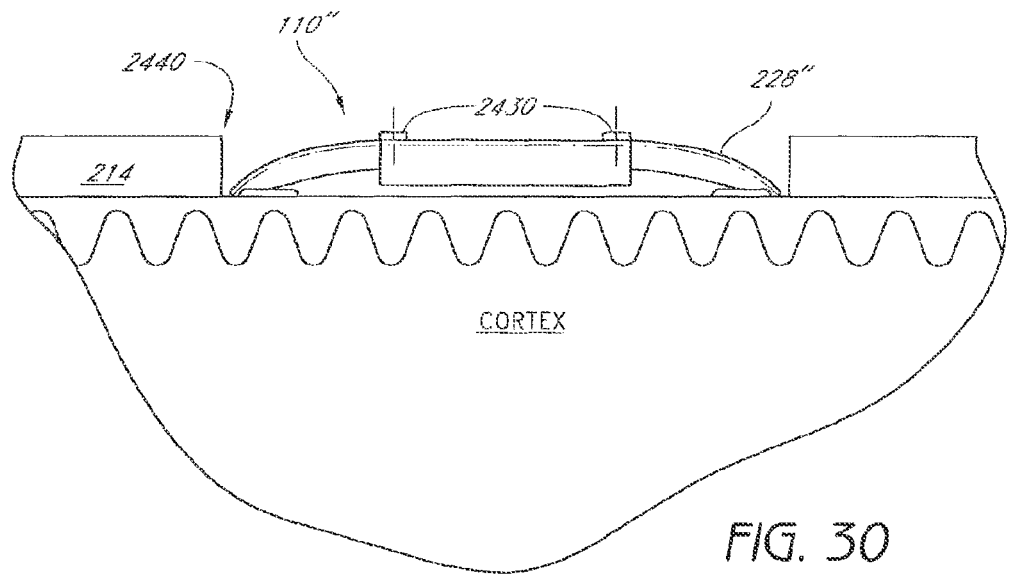
FIG. 30 is a schematic side elevational view and partial sectional view of a patient's skull in which the implantable recording device is installed.
Figure 31:
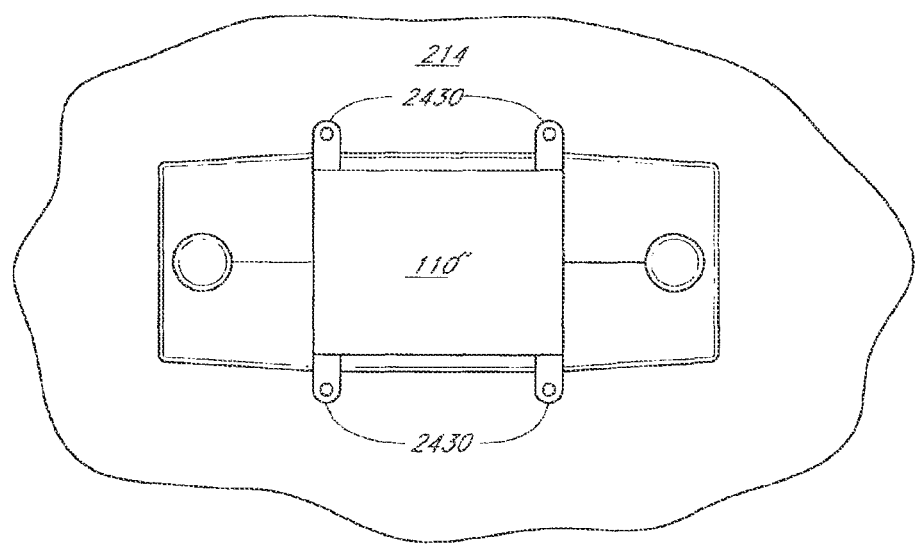
FIG. 31 is a top plan schematic view of a patient's skull in which the implantable recording device of FIG. 27 is installed.

FIGS. 30 and 31, illustrate an exemplary but nonlimiting mounting position for the recording device 110". In this installation, the patient has been given a craniotomy which forms an installation site 2440.

The recording device 110" is placed within the installation site 2440 such that the mounting tabs 2430 extend over an outer surface of the cranium 214. In this position, screws can be inserted through the apertures defined in the mounting tabs 2430 and into the cranium 214. As such, the recording device 110" can be better secured in place and maintained within the installation site 2440.

Additionally, because of the inclusion of the cushioning member 228", the recording device 110" better conforms to the arching configuration of the installation site 2440, and more are particularly, the outer surface of the cortex. Thus, the recording device 110" can be more comfortable for the patient.

Figure 32:
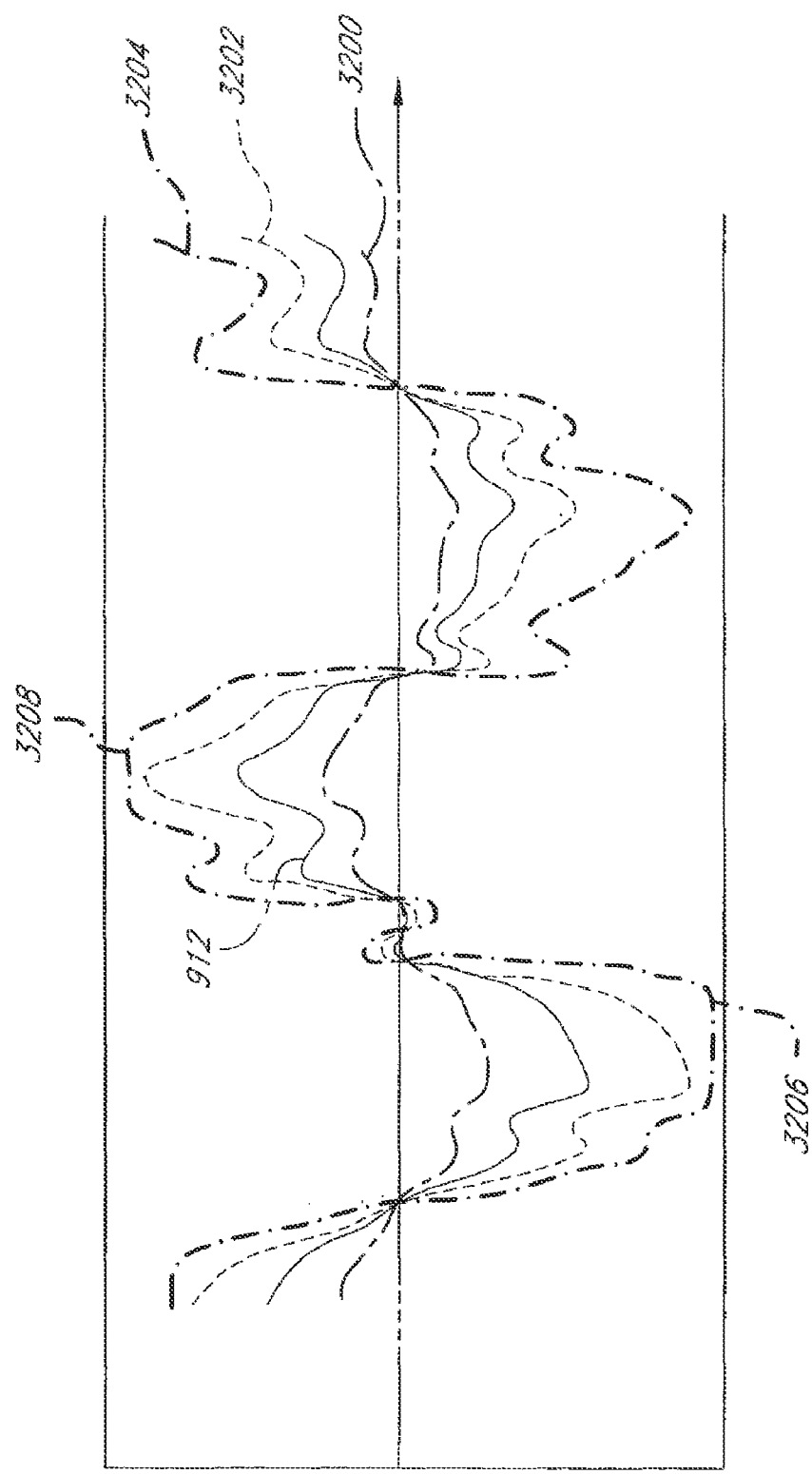
FIG. 32 is a schematic representation of a patient's brainwaves and illustrates various stages of adjustment of an amplifier with in the implantable recording device.

After a recording device, such as the recording devices 110, 110', 110", have been implanted in a patient, the amplifiers 610 within such recording devices can be adjusted. For example, FIG. 32 illustrates the filtered voltage 912 described above with reference to FIG. 9. The filtered voltage 912 is an example of a filtered voltage that can be recorded or analyzed for purposes of diagnosis of epileptic seizures, or other disorders.

However, when devices such as on of the recording devices 110, 110', 110" is first installed, the maximum amplitudes of voltages detected by the sensors 412, 414 cannot be predicted. Thus, after the initial installation of such a device, amplifier adjustments can be made so that the voltages output from the amplifier 610 are within a normal operation range for the amplifier 610, and such that the voltage output from the amplifier 610 does not reach the maximum output voltage of the amplifier 610 an excessive number of times.

For example, FIG. 32 illustrates voltage traces of several other exemplary outputs from the amplifier 610. The voltage traces 3200, 3202, and 3204 are examples of the output of the amplifier 610 at different gain settings. The amplifier 610 can be any type of amplifier. Preferably, however, the amplifier 610 has an adjustable gain. In some embodiments, the adjustable gain feature is provided through the use of a variable resistor. However, any type of adjustable gain amplifier can be used.

In FIG. 32, the voltage trace 3204 is an example of the filtered output of the amplifier 610 having been adjusted to its maximum gain. As reflected in the voltage trace 3204, the amplifier 610 reaches its saturation point and thus, the voltage trace 3204 reaches and remains constant at maximum voltage portions 3206 and 3208. Assuming that the brainwaves generating this voltage signal are normal, i.e., not indicative of epileptic seizures, it is undesirable for the amplifier 610 to reach its saturation point frequently. For example, in some embodiments, it is acceptable if the voltage output from the amplifier 610 reaches its saturation point no more than about once per second.

However, if the amplifier 610 reaches its saturation point and thus outputs maximum or minimum voltages more than about once per second during normal brainwave activity, then the gain of the amplifier 610 may be too high. Thus, the gain of the amplifier 610 can be reduced until the signal output from the amplifier 610 reaches its maximum or minimum values no more than about once per second. After the gain of the amplifier 610 has been adjusted as such, the recording devices 110, 110', 110", can be used for the diagnostic uses noted above.

One way for performing such a calibration procedure is to install a recording device, such as any of the recording devices 110, 110', 110", with the amplifier 610 adjusted to its maximum gain value. This is because it is difficult to predict, as noted above, how strong the raw detected brainwave signals will be.

With the amplifier 610 adjusted to its maximum gain value, the patient can be released for an amount of time that will allow the patient to have several or more seizures. After such a time has expired, the patient can return so that a practitioner can read the information stored in the memory device 516 of the recording devices 110, 110', 110", to determine if the gain of the amplifier 610 was sufficiently high.

Reviewing the brainwave signals recorded by the recording devices 110, 110', 110", will reveal to a practitioner whether or not the gain of the amplifier 610 was sufficiently high. For example, practitioners can distinguish between brainwaves indicating normal brainwave activity and brainwaves indicating epileptic seizures. Thus, if the data recorded by the recording device 110 includes numerous and high frequency occurrences of the amplifier 610 reaching its saturation point during normal brainwave activity, the gain of the amplifier 610 was too high. As such, the practitioner can, using for example the control interface 518 (FIG. 5), reduce the gain of the amplifier 610. If, on the other hand, the practitioner determines that the gain of the amplifier 610 was not high enough, for example, if the amplifier 610 never reaches its saturation point, and us the voltage output from the amplifier 610 never reaches a maximum voltage level, then the gain of the amplifier 610 may be too low. Thus, the practitioner, using the control interface 518, can raise the gain of the amplifier 610.

Figure 34:
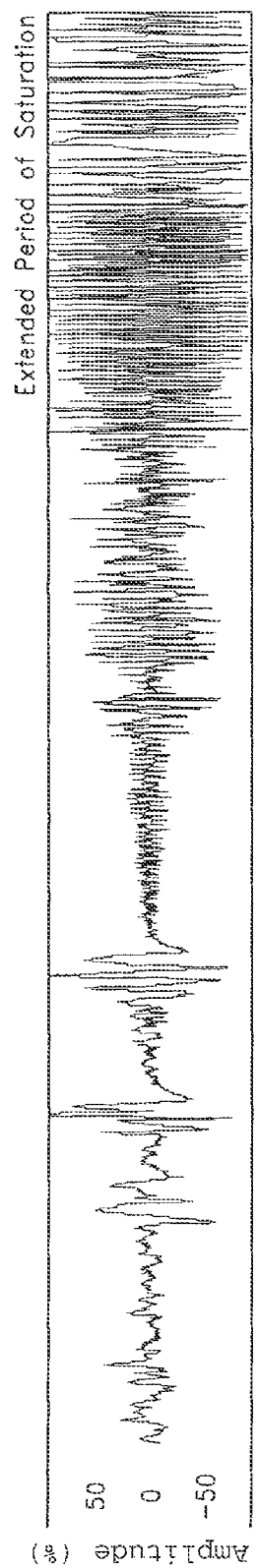
FIG. 34 is an exemplary depiction of a patient's brainwaves detected by a detection device and including an extended period during which an amplifier in the detection device is saturated.

When a seizure occurs, the EEG waveform typically appears as a reciprocating waveform that reaches saturation voltage for an extended period of time, for example, as shown in FIG. 34. The time at which the EEG reaches saturation voltage will depend on the gain setting with higher gain settings producing earlier but more frequent saturation events.

Figure 35:
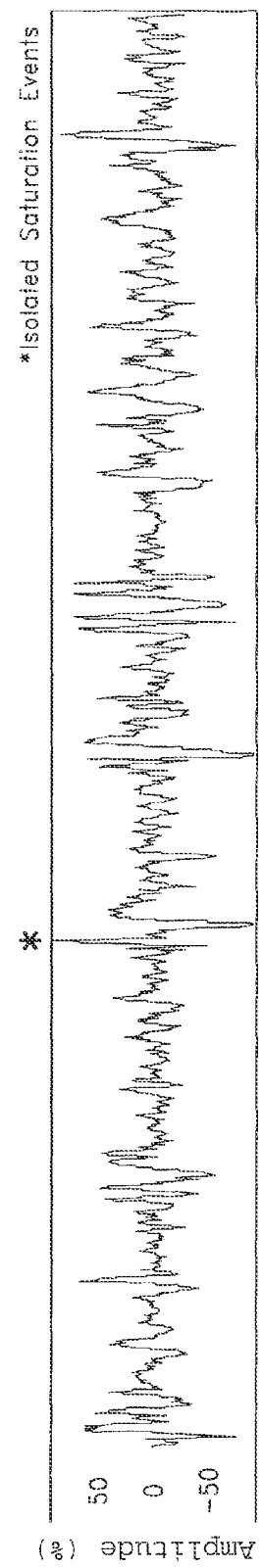
FIG. 35 is another exemplary depiction of a patient's brainwaves detected by a detection device and including only isolated events during which an amplifier in the detection device is saturated.

Interictal (non-seizure) baseline EEG can also have brief periods of saturation that may be abnormal as shown in FIG. 35 (marked by *). The practitioner may not want to have these brief saturation events reported because they do not represent seizures or other significant neurological events and they can occur quite frequently. Therefore, the device 110 should be able to distinguish between sustained periods of saturation that may be neurological events of clinical significance and brief periods of saturation that may be frequent and not of clinical significance.

Figure 33:
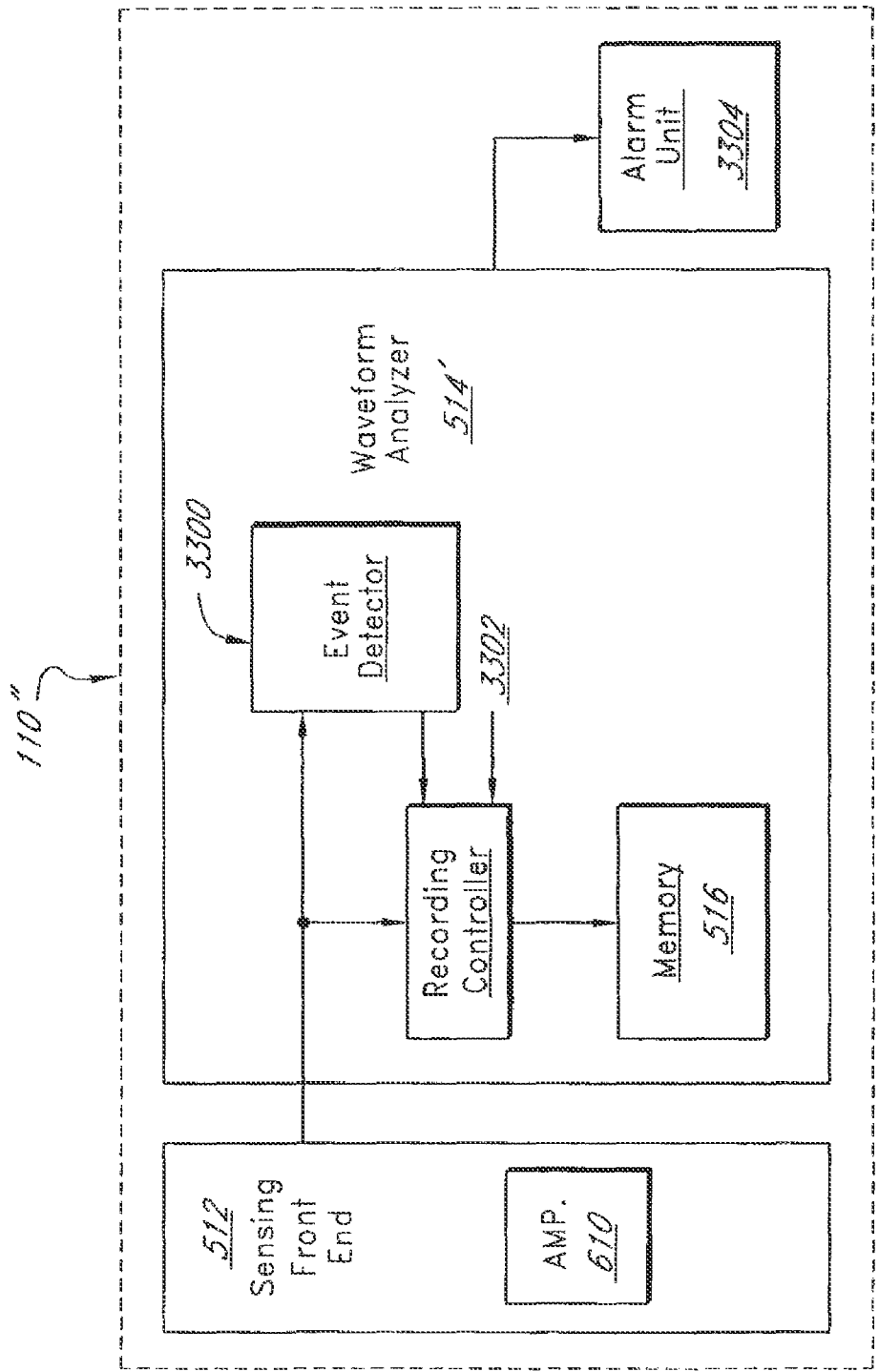
FIG. 33 is a schematic illustration of a modification of a waveform analyzer that can be included in any of the implantable recording devices illustrated in the above figures.

For example, with reference to FIG. 33, a modification of the waveform analyzer 514 (FIG. 5) is illustrated therein and identified generally by the reference to numeral 514'. The waveform analyzer 514' includes some components that can be constructed in accordance with the description noted above with respect to the analyzer 514. Other components of the analyzer 514' also correspond to components of the analyzer 514 but include modifications. As such, those components are identified with the same reference 8 used in the description of the analyzer 514 except that a "'" has been added thereto.

As shown in FIG. 33, the waveform analyzer 514' can include an event detector 3300, a recording controller 3302 and a memory device 516. However, the waveform analyzer 514' can also include other devices.

Figure 36:
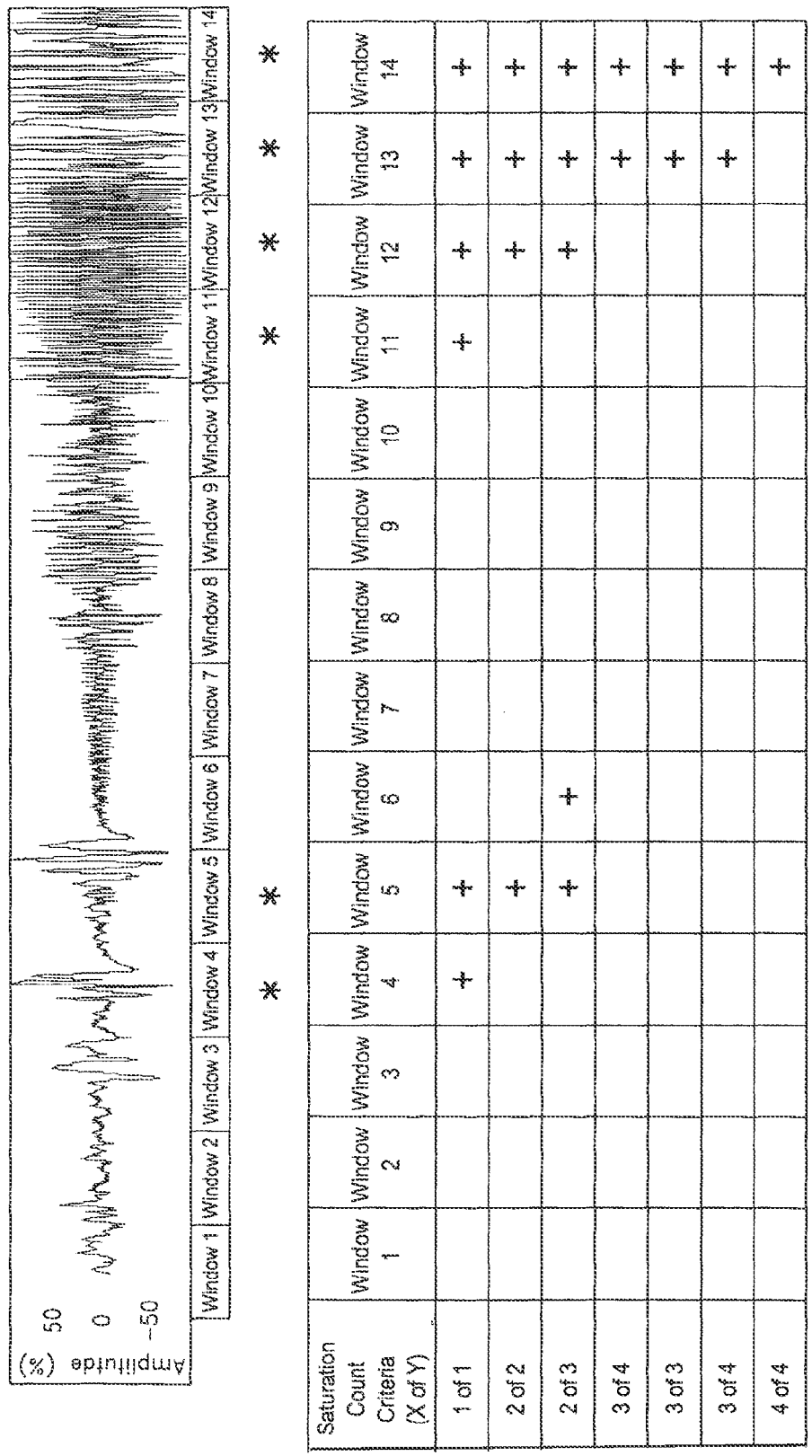
FIG. 36 includes, in an upper portion, the depiction of a patient's brainwaves from FIG. 34, broken down into windows, and a table, in a lower portion, tabulating saturation count criteria for each window.

In some embodiments, the event detector 3300 can be programmed to determine whether saturation is occurring at a predetermined rate and/or for a predetermined sustained period of time. An exemplary waveform of significant neurological event is shown in FIG. 36. The waveform data in FIG. 36 has been subdivided into a series of windows (labeled 1-14 in FIG. 36), which can be of any programmable length, but, in some embodiments can be 25-1000 msec. These windows can overlap, but are shown as non-overlapping in FIG. 36.

The waveform analyzer 514 can be configured to determine if any data point within any window is saturated. In the representative waveform in FIG. 36, an asterisk below the respective windows indicate which windows have a saturated data point.

In some embodiments, the practitioner can program the event detector 3300 with regard to how many windows within a continuous subset would need to have a saturated data point in order for the event detector to determine that a seizure has occurred. For example, the practitioner could specify that X out of Y contiguous windows would be required to have a saturated event (where Y is always greater or equal to X) for the event detector 3300 to determine a seizure or significant neurological event has occurred.

The table in FIG. 36 shows various outcomes for different saturation count criteria X and Y values for the representative waveform (a "+" in a table block indicates that detection has occurred). These types of detections are referred to as X/Y saturation detections.

In some embodiments, the event detector 3300 can be configured to determine whether a seizure or other neurological event has occurred based upon analyses of X/Y saturation detections. In such embodiments, the event detector 3300 can be programmed to determine how frequently X/Y saturation detections are occurring and then only report neurological events to the practitioner if the X/Y saturation rate exceeds a certain rate of occurrence. For example, the detector 3300 can be configured to monitor the number of times that the X/Y saturation criteria were met in a programmable time window, but then only report an event to the practitioner if a minimum number of programmable X/Y saturation events were detected in a programmable time period.

For example, the detector 3300 can be programmed with a time window of 5 minutes and an X/Y saturation count criterion of 5. The detector would then only report a neurological event to the practitioner if 5 or more X/Y saturation events were to have occurred in the past 5 minutes.

The recording controller 3302 can be configured to record and store recordings of the patient's brainwaves under certain circumstances. In some embodiments, the recording controller 3302 can be configured to utilize the memory device 516 to serve as a linear cache and a file storage unit.

For example, in various other areas in the signal processing arts, a linear cache is a known device for storing a single stream of digital information in a proper sequence. As such, the linear cache maintains this stream as a list of the digital blocks that make up to stream. In some embodiments, the digital blocks can each have a unique size and unique attributes, or the blocks can have a predetermined size, for example corresponding to a predetermined period of time such as 1 second, 5 five seconds, 10 seconds, 30 seconds, etc. However, the blocks can have any size. Each block within the stream can be marked with a "presentation timestamp" which indicates when that block should be presented to a decoding process.

The presentation timestamp can be a monotonically increasing in value initialized at zero when the linear cache first begins operation on a stream of data. In some embodiments, the presentation timestamp generates its own time stamp signature without any relation to any other underlying clocking or streaming technique. The technique used for generating the presentation timestamp is also utilized by any decoding process used to read the digital blocks in the order recorded.

In some embodiments, the recording controller 3302 time stamps each encoded digital block of data from the sensing front end device 512 as it arrives at the recording controller 3302. In other words, the recording controller 3302 marks that block of data with the current presentation timestamp for the stream of data being recorded.

The recording controller 3302 can be configured to maintain a window of blocks in a window cache, for example. The recording controller 3302 can form a window cache of digital blocks, in the order according to the presentation timestamp values. As such, the window can contain the newest block that arrived in the window cache of digital blocks and the oldest block that this window cache is configured to hold. The window cache can be configured to hold any number of digital blocks.

For example, the window cache can be configured to hold the number of digital blocks corresponding to the amount of time to equal to 10 seconds, 30 seconds, 1 minute, 10 minutes, 30 minutes, 60 minutes, or any amount of time. In some embodiments, the recording controller 3302 can have an adjustable window size allowing a practitioner to adjust the duration of the window size which the window cache will hold. This allows the practitioner to adjust the length of the recorded brainwaves before a seizure is detected and after a seizure is detected.

In other words, the window cache of digital blocks represents a time span into the past history of the stream of brainwaves coming from the sensing front-end 512. The recording controller 3302 can be configured to discard digital blocks that fall outside the window cache. In other words, the recording controller 3302 can be configured to erase digital blocks that fall outside of the window cache. As such, the window is sized such that one can only look back a limited distance into the past history of the datastream output from the sensing front and 512. This allows for trade-offs between the available storage space and the availability of past information for storing.

Additionally, in some embodiments, the recording controller 3302 can be configured to store all or a portion of the digital blocks stored within the cache window into a file when the event detector 3300 indicates that a seizure or other event has occurred. In some embodiments, the recording controller 3302 can be configured to store all of the digital blocks held in the window cache in a file when the event detector 3300 indicates the seizure has begun or occurred and to continue to add digital blocks to the file for an amount of time after the event detector 3300 indicates the seizure has been detected. In some embodiments, the recording controller 3302 can be configured to continue recording the output from the sensing front and 512 until the event detector 3300 indicates that the seizure has ended. Further, in some embodiments, the recording controller 3300 can be configured to continue to add digital blocks to the file for a predetermined time after the event detector 3300 indicates that the seizure has ended.

Optionally, the recording controller 3302 can be configured to save only a number of digital blocks within the window, at the time detent detector 3300 indicates the seizure has begun, corresponding to a predetermined time before the event detector 3300 indicates the seizure has begun. This predetermined time can be any predetermined time. For example, but without limitation, this predetermined time can be equal to 10 seconds, 30 seconds, 60 seconds, or any predetermined amount of time. Additionally, in some embodiments, the recording controller 3302 can be configured to allow this predetermined time to be adjusted by a practitioner.

After the recording controller 3302 has collected all the digital blocks surrounding the detection of a seizure by the event detector 3300 and to include the digital blocks corresponding to the predetermined time periods before and after the event detector 3300 indicates a seizure has occurred, the recording controller 3302 can save the file including these blocks into the memory device 516. Additionally, the recording controller 3302 can stamp the file with the date and time for further analysis by a practitioner. As such, the waveform analyzer 514' provides additional advantages in the ability to more simply distinguish between normal brain activity and brain activity associated with the seizure and to save the relevant portions of the brainwave signals received from the sensing front and 512 in a more efficient manner thereby saving memory and reducing power consumption.

The above described method for generating files of selected portions of detected brainwave activity can be incorporated into any of the other recording devices 110, 110', 110" described above or below.

Such a method for storing selected portions of detected brainwave activity can also aid in the process of calibrating the amplifier 610. For example, after the initial installation of a recording device, such as any of the recording devices 110, 110', 110", 110''', and preferably after the patient has suffered one or more seizures, the files containing the selected portions of detective brainwave activity can be reviewed by a practitioner. An ordinary practitioner can readily identify whether or not these files of selected brainwave activity include brainwave activity resulting from a seizure.

If the practitioner determines that the files do not contain brainwaves resulting from seizure activity, the practitioner can use the recordings to determine what adjustments to make to the recording device 110. For example, the practitioner may determine that it is necessary to adjust the gain of the amplifier 610, or to make other adjustments.

In some embodiments, any of the recording devices 110, 110', 110", can include an alarm unit 3304 configured to provide a tactile stimulus to the patient in which the recording device is installed. For example, the alarm unit 3304 can include a speaker, vibrator, bone conduction speaker, or any other device that can provide a tactile stimulus to the patient. As such, this provides an additional advantage that the patient can be made aware that the recording device should be checked by practitioner.

For example, the power supply 432 (FIG. 4) might need to be replaced. The memory device 516 might be full and thus not able to store or any further information regarding detected seizures.

However, the alarm unit 3304 can be used to communicate with the patient 112 for any reason. In an exemplary but nonlimiting embodiment, the alarm unit 3304 can emit audible beeps to the patient 112 if the recording device 110 should be checked by practitioner. For example, the alarm unit 3304 can be configured to emit 1 beep periodically to indicate that the patient 112 should contact their practitioner at their earliest convenience. Additionally, the alarm unit 3304 can be configured to emit two beeps periodically to indicate that the patient 112 should visit their practitioner as soon as possible. Other communication schemes can also be used.

An implantable version of a system according to some embodiments advantageously has a long-term average current consumption significantly less than 10 microamps, allowing the implanted device to operate on power provided by a coin cell or similarly small battery for a period of years without need for replacement. It should be noted, however, that as battery and power supply configurations vary, the long-term average current consumption of a device according to some embodiments may also vary and still provide satisfactory performance.

It should be observed that while the foregoing detailed description of various embodiments of the present inventions is set forth in some detail, the present inventions are not limited to those details and an implantable recording device 110 or neurological disorder detection device made according to the inventions can differ from the disclosed embodiments in numerous ways. In particular, it will be appreciated that embodiments of the present inventions may be employed in many different applications to detect anomalous neurological characteristics in at least one portion of a patient's brain. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the inventions may not be drawn along the same boundaries. Hence, the appropriate scope hereof is deemed to be in accordance with the claims as set forth below.

What is claimed is:

1. A method for detecting neurological events comprising:
sensing brainwaves of a patient;
generating a signal indicative of the sensed brainwaves;
amplifying the signal in an amplifier, the amplifier having a gain adjustable to predetermine an amplitude of the signal that will place the amplifier in saturation; and
determining, by a processor, if a neurological event has occurred based on occurrences of saturation of the amplifier.

2. The method according to claim 1, wherein determining, by the processor, if the neurological event has occurred includes determining if the neurological event has occurred based on the frequency at which the amplifier saturates.

3. The method according to claim 1, wherein determining, by the processor, if the neurological event has occurred includes determining if the neurological event has occurred based on the number of times the amplifier saturates in a predetermined number of time windows.

4. The method according to claim 1, wherein determining, by the processor, if the neurological event has occurred includes:
determining, for each time window in a plurality of contiguous time windows, whether the amplifier is saturated; and
determining whether a ratio of a number of time windows in which the amplifier is saturated and the number of contiguous time windows exceeds a predetermined ratio.

5. A method for calibrating an implantable device including an adjustable gain amplifier, the method comprising:
setting an initial gain of the amplifier;
sensing brainwaves of a patient using the implantable device;
generating a signal indicative of the sensed brainwaves using the implantable device;
amplifying the signal in an amplifier, the amplifier having a gain adjustable to predetermine an amplitude of the signal that will place the amplifier in saturation;
determining, by a processor, occurrences of saturation of the amplifier during normal brain activity;
determining, by the processor, whether the occurrences of saturation of the amplifier during normal brain activity exceed a threshold;
adjusting the gain of the amplifier if the occurrences of saturation of the amplifier during normal brain activity exceed the threshold;
repeating determining, by the processor, occurrences of saturation of the amplifier during normal brain activity;
determining, by the processor, whether the occurrences of saturation of the amplifier during normal brain activity exceed the threshold, and adjusting the gain, until the occurrences of saturation of the amplifier during normal brain activity do not exceed the threshold; and
if the occurrences of saturation of the amplifier during normal brain activity do not exceed the threshold, determining, by the processor, if a neurological event has occurred based on occurrences of saturation of the amplifier.

6. The method of claim 5, wherein determining, by the processor, whether the occurrences of saturation of the amplifier during normal brain activity exceed a threshold includes determining whether a number of saturations of the amplifier exceeds a threshold number of times during a time interval.

7. The method of claim 5, wherein the initial gain is a maximum gain value of the amplifier.

8. The method of claim 7, wherein adjusting the gain of the amplifier includes reducing the gain of the amplifier.

9. The method of claim 5, further comprising storing the occurrences of saturation of the amplifier during normal brain activity.

10. The method of claim 9, wherein determining, by the processor, whether the occurrences of saturation of the amplifier during normal brain activity exceed a threshold includes determining whether the stored occurrences of saturation of the amplifier during normal brain activity exceed the threshold.

11. The method of claim 5, further comprising:
determining, by the processor, whether the occurrences of saturation of the amplifier during normal brain activity does not exceed a minimum value; and
increasing the gain of the amplifier if the occurrences of saturation of the amplifier during normal brain activity does not exceed the minimum value, wherein the repeating includes determining, by the processor, whether the occurrences of saturation of the amplifier during normal brain activity does not exceed a minimum value and increasing the gain of the amplifier.

* * * * *